(12) United States Patent
Kuipers

(10) Patent No.: US 10,501,514 B2
(45) Date of Patent: Dec. 10, 2019

(54) CYCLIC GALANIN-ANALOGS AND USES THEREOF

(71) Applicant: LanthioPep B.V., Groningen (NL)

(72) Inventor: Anneke Kuipers, Haule (NL)

(73) Assignee: LANTHIOPEP B.V., Groningen (NL)

( * ) Notice: Subject to any disclaimer, the term of this patent is extended or adjusted under 35 U.S.C. 154(b) by 18 days.

(21) Appl. No.: 15/557,273

(22) PCT Filed: Mar. 11, 2016

(86) PCT No.: PCT/EP2016/055266
§ 371 (c)(1),
(2) Date: Sep. 11, 2017

(87) PCT Pub. No.: WO2016/146513
PCT Pub. Date: Sep. 22, 2016

(65) Prior Publication Data
US 2018/0057556 A1    Mar. 1, 2018

(30) Foreign Application Priority Data

Mar. 13, 2015 (EP) .................................... 15159102

(51) Int. Cl.
| | | |
|---|---|---|
| A61K 38/00 | (2006.01) | |
| C07K 14/575 | (2006.01) | |
| A61K 47/54 | (2017.01) | |
| A61K 38/22 | (2006.01) | |
| C07K 1/04 | (2006.01) | |
| C07K 1/107 | (2006.01) | |

(52) U.S. Cl.
CPC ............ C07K 14/575 (2013.01); A61K 38/22 (2013.01); A61K 47/549 (2017.08); C07K 1/04 (2013.01); C07K 1/1075 (2013.01); C07K 2319/02 (2013.01); C07K 2319/50 (2013.01)

(58) Field of Classification Search
CPC .... A61K 38/22; A61K 47/549; C07K 14/575; C07K 1/04; C07K 1/1075; C07K 2319/02; C07K 2319/50
See application file for complete search history.

(56) References Cited

FOREIGN PATENT DOCUMENTS

| | | |
|---|---|---|
| WO | WO99/05302 | 2/1999 |
| WO | WO03/099863 | 12/2003 |

OTHER PUBLICATIONS

Barblivien et al. "Galanin inhibits the vasodilatatory basalocortical cholinergic system in the anaesthetized rat" Neuroreport 1995 6:1849-1852.

Barreto et al. "Galanin receptor 3—a potential target for acute pancreatitis therapy" Neurogastroenterol Motil 2011 23(3):e141-51.
Botella et al. "Galanin contracts and relaxes guinea pig and canine intestinal smooth muscle cells through distinct receptors" Gastroenterology 1995 108:3-11.
Carpenter et al. "The glycine residue in cyclic lactam analogues of galanin(1-16)-NH2 is important for stabilizing an N-terminal helix" Biochem. 1999 38:15295.
Elliott-Hunt et al. "Activation of the galanin receptor 2 (GalR2) protects the hippocampus from neuronal damage" J Neurochem 2007 100:780-9.
Green et al. "Cyclic analogs of galanin and neuropeptide Y by hydrocarbon stapling" Bioorg Med Chem. Jan. 1, 2013;21(1):303-10.
Gross, K.J. & Pothoulakis, C. "Role of Neuropeptides in Inflammatory Bowel Disease" Inflamm Bowel Disease 2007 13:918-32.
Hokfelt, T. & Takemoto, K. "Galanin—25 years with a multitalented neuropeptide" 2008 Cell Mol Life Sci 65:1793-5.
Hokfelt, T. "Galanin and its receptors: Introduction to the Third International Symposium, San Diego, California, USA, Oct. 21-22, 2004" Neuropeptides 2005 39:125.
Jensen, P.R. & Hammer, K. "Minimal Requirements for Exponential Growth of Lactococcus lactis" Appl Environ Microbiol 1993 59: 4363-6.
Kluskens et al. "Post-translational Modification of Therapeutic Peptides by NisB, the Dehydratase of the Lantibiotic Nisin" Biochemistry 2005 44:12827-12834.
Kluskens et al. "Angiotensin-(1-7) with Thioether Bridge: an Angiotensin Converting Enzyme-Resistant, Potent Angiotensin-(1-7) analog" J. Pharmacol. Exper. Ther. 2009 328:849-854.
Kuteeva et al. "Galanin, galanin receptor subtypes and depression-like behavior" Cell Mol Life Sci 2008 65, 1854-63.
Lerner et al. "Galanin and epilepsy" Cell Mol Life Sci 2008 65:1864-71.
Lu et al. "Distribution and differential regulation of galanin receptor subtypes in rat brain: effects of seizure activity" Neuropeptides 2005 39:147-52.
Lu, X. "GalR2-positive allosteric modulator exhibits anticonvulsant effects in animal models" PNAS 2010 107:15229-34.
Mitsukawa et al. "Galanin, galanin receptors, and drug targets" Experentia Supplementation 2010 102:7-23.
Rink et al. "Lantibiotic structures as guidelines for the design of peptides that can be modified by lantibiotic enzymes" Biochemistry 2005 44:8873-82.
Rink et al. "NisC, the cyclase of the lantibiotic nisin, can catalyze cyclization of designed non-lantibiotic peptides" Biochemistry 2007 46:13179-13189.
Rink et al. "To protect peptide pharmaceuticals against peptidases" Journal of Pharmacological and Toxicological Methods 2010 61:210-218.

(Continued)

Primary Examiner — Thomas S Heard
(74) Attorney, Agent, or Firm — Licata & Tyrrell P.C.

(57) ABSTRACT

The invention generally relates to the field of medicine and pharmacology. More particularly, it relates to novel analogs of galanin, and the use thereof in therapy. Provided is a cyclic peptide analog of galanin, wherein the galanin analog comprises a (methyl)Lanthionine bridge and wherein the analog has the general formula "X1-X2-X3-X4-X5-X6-X7-X8-X9-X10-X11-X12-X13-X14-X15-X16-X17-X18-X19-X20-X21-X22-", or a truncated variant thereof lacking X1 and/or up to 11 of the C-terminal residues, wherein two residues selected from the group consisting of X3, X4, X6, X7, X10 and X13-X19 together form a Lanthionine bridge of the structure Ala-S-Ala, or a methyl Lanthionine bridge of the structure Abu-S-Ala or Ala-S-Abu.

5 Claims, 3 Drawing Sheets

Figure 1:
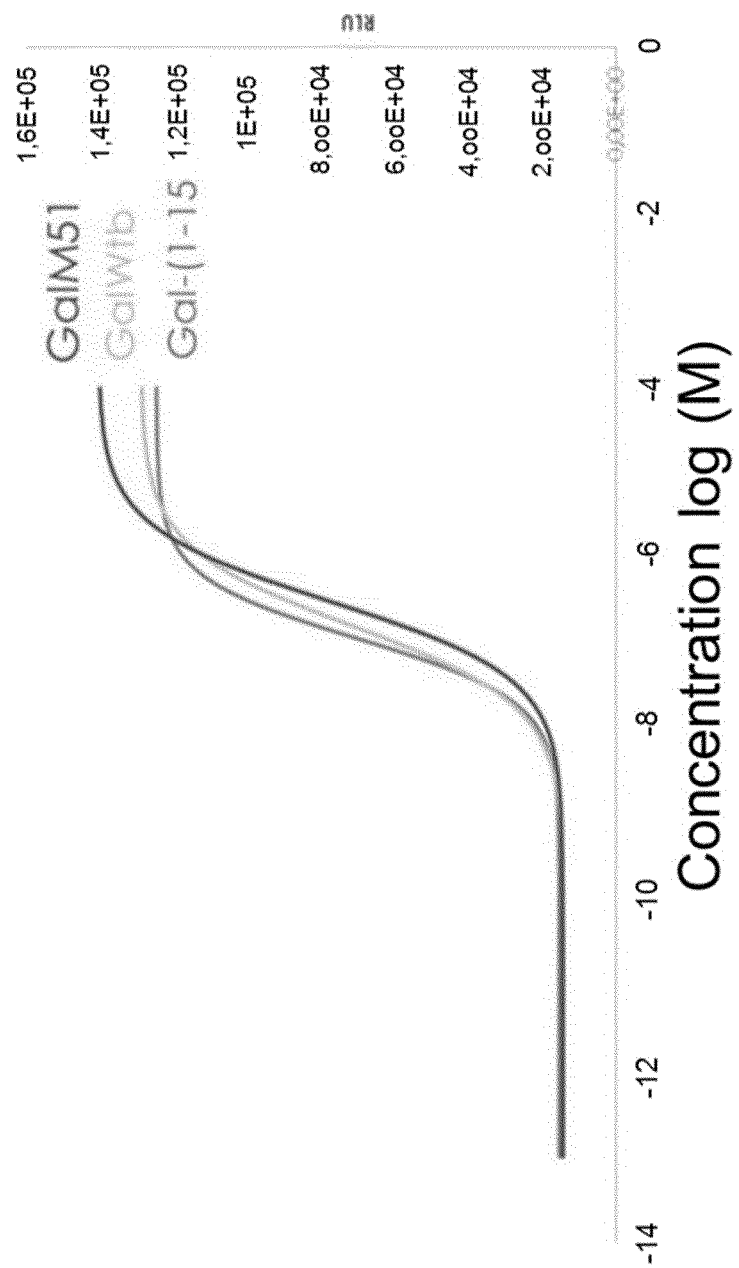

Specification includes a Sequence Listing.

(56) References Cited

OTHER PUBLICATIONS

Robertson et al. "Engineering Galain Analalogues that Discriminate Between GalR1 and Gal R2 Receptor Subtypes and Exhibit Anticonvulsant Activity Following Systemic Delivery" Journal Med. Chem. 2010 53(4):1871-1875.
Saar et al. "Novel galanin receptor subtype specific ligands in feeding regulation" Neurochemistry Int 2011 58: 714-20.
Sollenberg et al. "Binding of Chimeric Peptides M617 and M871 to Galanin Receptor Type 3 Reveals Characteristics of Galanin Receptor-Ligand Interaction" Int J Pept Res Ther 2010 16:17.
Swanson et al. Anxiolytic- and antidepressant-like profiles of the galanin-3 receptor ($Gal_3$) antagonists SNAP 37889 and SNAP 398299 PNAS 2005 102:17489-94.
Tang et al. "$G_o2$ G protein mediates galanin inhibitory effects on insulin release from pancreatic β cells" PNAS 2012 109:2636-41.
Wraith et al. "A role for galanin in human and experimental inflammatory demyelination" PNAS 2009 106:15466-71.
Zhang et al. "Galanin transgenic mice with elevated circulating galanin levels alleviate demyelination in a cuprizone-induced MS mouse model" PLoS One. 2012 7(3):e33901.
International Search Report and Written Opinion in PCT/EP2016/055266 dated Jun. 28, 2016.
International Preliminary Report on Patentability in PCT/EP2016/055266 dated Sep. 19, 2017.

CYCLIC GALANIN-ANALOGS AND USES THEREOF

This patent application is the U.S. National Stage of International Application No. PCT/EP2016/055266 filed Mar. 11, 2016, which claims the benefit of EP 15159102.1 filed Mar. 13, 2015, each of which is incorporated by reference in its entirety.

The invention generally relates to the field of medicine and pharmacology. More particularly, it relates to novel analogs of galanin, methods for producing them, and the use thereof in therapy.

Galanin is a neuropeptide consisting of a chain of 29-30 amino acids produced from the cleavage of a 123-amino acid protein known as preprogalanin, which is encoded by the GAL gene. It is widely expressed in the brain, spinal cord, and gut of humans as well as other mammals. Galanin has been implicated in many biologically diverse functions, including: nociception, waking and sleep regulation, cognition, feeding regulation, regulation of mood, regulation of blood pressure, it also has roles in development as well as acting as a trophic factor. Galanin is linked to a number of diseases including Alzheimer's disease, epilepsy as well as depression, eating disorders and cancer.

Galanin stimulates three receptor subtypes, GalR1, GalR2 and GalR3 [Mitsukawa K, 2010 Galanin, galanin receptors, and drug targets. EXS 102, 7-23]. There are differences in distribution and pathways between these subtypes.

Gal R1 is expressed in basal forebrain, hypothalamus, spinal cord and colonic epithelial cells where it is upregulated in the case of inflammatory bowel disease (IBD). Not much is known about the effects following stimulation of GalR1. Stimulation of GalR1 seems to be involved in feeding [Saar I, 2011 Novel galanin receptor subtype specific ligands in feeding regulation. Neurochemistry Int 58, 714-20].

GalR2 is widely distributed in brain, but also occurs in pituitary gland and peripheral tissues. Stimulation of GalR2 has been reported to be neuroprotective in case of MS [Wraith D C, 2009 A role for galanin in human and experimental inflammatory demyelination PNAS 106, 15466-71; Zhang L, 2012 Galanin transgenic mice with elevated circulating galanin levels alleviate demyelination in a cuprizone-induced MS mouse model. PLoS One. 7(3):e33901] and Alzheimer and to have anxiolytic, antidepressant and anticonvulsant effects.

GalR3 is widely distributed at low abundance [Lu X, 2005 Distribution and differential regulation of galanin receptor subtypes in rat brain: effects of seizure activity. Neuropeptides 39, 147-52; Mitsukawa K, 2010 Galanin, galanin receptors, and drug targets. EXS 102, 7-23; Hokfelt T, 2008 Galanin—25 years with a multitalented neuropeptide. Cell Mol Life Sci 65, 1793-5; Hokfelt T 2005 Galanin and its receptors: Introduction to the Third International Symposium, San Diego, Calif., USA, 21-22 Oct. 2004. Neuropeptides 39, 125; Kuteeva E, 2008 Galanin, galanin receptor subtypes and depression-like behavior. Cell Mol Life Sci 65, 1854-63Mol Life Sci 65, 1842-53]. Only little information is available on ligand receptor Gal3 interaction [Sollenberg U E, 2010 Binding of Chimeric Peptides M617 and M871 to Galanin Receptor Type 3 Reveals Characteristics of Galanin Receptor-Ligand Interaction. Int J Pept Res Ther 16, 17].

Taken together, while effects of stimulation of GalR1 and GalR3 seem unknown or are unbeneficial, agonistic stimulation of GalR2 appears effective in case of MS [Wraith D C, 2009 A role for galanin in human and experimental inflammatory demyelination. PNAS 106, 15466-71; Zhang L, 2012 Galanin transgenic mice with elevated circulating galanin levels alleviate demyelination in a cuprizone-induced MS mouse model. PLoS One. 7(3):e33901].

GalR2 stimulation leads to neuroprotection [Elliott-Hunt C R, 2007 Activation of the galanin receptor 2 (GalR2) protects the hippocampus from neuronal damage. J Neurochem 100, 780-9] and anticonvulsant activities [Lu X, 2010 GalR2-positive allosteric modulator exhibits anticonvulsant effects in animal models. PNAS 107, 15229-34]. Galanin appears to exert these anticonvulsant effects through both type 1 and type 2 receptors, with distinct downstream signaling cascades [Lerner J T, 2008 Galanin and epilepsy. Cell Mol Life Sci 65, 1864-71 Neurochem 100, 780-9]. The GalR2 linked G(o)2 mediates the inhibition of insulin release by galanin by regulating both K(ATP) and Ca(2+) channels in mice [Tang G, 2012 Go2 G protein mediates galanin inhibitory effects on insulin release from pancreatic δ cells. PNAS 109, 2636-41]. With respect to safety it seems that agonistic specificity for GalR2 and reduced agonistic specificity for GalR3 might be relevant. The main signaling for GALR2 is via Gq through the phospholipase C/protein kinase C pathway, which is not stimulated via GalR1 or GalR3. However, it has been demonstrated that GalR2 can also couple to Gi proteins to inhibit adenylate cyclase, like GalR1 and GalR3; and can also stimulate MAPK.

The present inventors recognized the need for galanin analogs that display differential pathway activation such that, according to needs, therapeutically relevant pathway(s) can be selectively stimulated. They therefore set out to design novel receptor subtype selective, systemically active, galanin receptor ligands. More specifically, they aimed at providing galanins agonistically acting via GalR2, and/or GalR1, while antagonistically, not or weakly agonistically acting via GalR3 in view of their therapeutic interest. In addition, it would be desirable to have galanins showing reduced capacity to induce receptor internalization, thus enhancing their (in vivo) efficacy.

It was surprisingly found that at least some of these goals could be met by the introduction of a lanthionine-ring in the galanin peptide. Without wishing to be bound by theory, it is thought that cyclization by the (methyl)lanthionine structure leads to a conformational constraint, which modulates galanine receptor subtype interaction. The (methyl)lanthionine can be introduced not only by replacing existing residues in the endogenous peptide sequence, but also by inserting amino acids.

Accordingly, the invention provides a cyclic peptide analog of galanin, wherein the galanin analog comprises a (methyl)lanthionine bridge and wherein the analog has the general formula "X1-X2-X3-X4-X5-X6-X7-X8-X9-X10-X11-X12-X13-X14-X15-X16-X17-X18-X19-X20-X21-X22 (SEQ ID NO:1), or a truncated variant thereof lacking X1 and/or up to 11 of the C-terminal residues, wherein two residues selected from the group consisting of X3, X4, X6, X7, X10 and X13-X19 together form a Lanthionine bridge of the structure Ala-S-Ala, or a methyl-Lanthionine bridge of the structure Abu-S-Ala or Ala-S-Abu, wherein:

X1 is pE, G, N, RGRG (SEQ ID NO:2), RGRGN (SEQ ID NO:3) or RGRGG (SEQ ID NO:4)
X2 is WN or WT
X3 is L, (me)lan, A, D, V, K, Q or N
X4 is N, T, Q or (me)lan
X5 is S or A
X6 is A or (me)lan
X7 is G, (me)lan, A or K
X8 is Y X9 is L
X10 is L, (me)lan or A
X11 is G, A or (me)lan
X12 is P or A or (me)lan
X13 is H, (me)lan, V, Q, P, Q, E, K or A
X14 is A, (me)lan, L, Q, P, H, K or I
X15 is V, (me)lan, P, F, G, K or A
X16 is (me)lan, P, F, L, N or G
X17 is N, (me)lan, P, G, S, A or H
X18 is H, (me)lan, A, L, P, A or R
X19 is R, (me)lan, L, M, F or A
X20 is R, A,
X21 is L, and
X22 is A,
in which
pE means pyroglutamate;
(me)lan means Lan or meLan, wherein Lan denotes the N- or C-terminal half of a Lanthionine (Ala-S-Ala) and meLan denotes the N- or C-terminal half of a methylLanthionine (Abu-S-Ala or Ala-S-Abu);
with the proviso that not more than two of X3, X4, X6, X7, X10 X11 and X13-X19 are (me)lan which together form a (methyl)Lanthionine bridge and wherein said (methyl)Lanthionine bridge is of the size i, i+3 or i, i+4 or i, i+5.

In another embodiment the invention provides a cyclic peptide analog of galanin, wherein the galanin analog comprises a (methyl)lanthionine bridge and wherein the analog has the general formula "X1-X2-X3-X4-X5-X6-X7-X8-X9-X10-X11-X12-X13-X14-X15-X16-X17-X18-X19-X20-X21-X22"     (SEQ ID NO:5), wherein two residues selected from the group consisting of X3, X4, X6, X7, X10 and X13-X19 together form a Lanthionine bridge of the structure Ala-S-Ala, or a methylLanthionine bridge of the structure Abu-S-Ala or Ala-S-Abu, and wherein:
X1 is pE, G, N, RGRG (SEQ ID NO:2), RGRGN (SEQ ID NO:3) or RGRGG (SEQ ID NO:4)
X2 is WN or WT
X3 is L, (me)lan, A, D, V, K or Q
X4 is N, T or (me)lan
X5 is S or A
X6 is A or (me)lan
X7 is G, (me)lan, A or K
X8 is Y
X9 is L
X10 is L, (me)lan or A
X11 is G, A or (me)lan,
X12 is P or A
X13 is H, (me)lan, V, Q, P, Q, E, K or A
X14 is A, (me)lan, L, Q, P, H, K or I
X15 is V, (me)lan, P, F, G, K or A
X16 is (me)lan, P, F, L or G,
X17 is N, (me)lan, P, G, S or A,
X18 is H, (me)lan, A, L, P or A,
X19 is R, (me)lan, L, M, F or A
X20 is R or A,
X21 is L
X22 is A
or a truncated variant thereof lacking X1 and/or up to 10 of the C-terminal residues,
in which pE means pyroglutamate (pGlu); (me)lan means Lan or meLan, wherein Lan denotes the N- or C-terminal half of a Lanthionine (Ala-S-Ala) and meLan denotes the N- or C-terminal half of a methylLanthionine (Abu-S-Ala or Ala-S-Abu);
with the proviso that not more than two of X3, X4, X6, X7, X10, X11 and X13-X19 are (me)lan which together form a (methyl)Lanthionine bridge and wherein said (methyl)Lanthionine bridge is of the size i, i+3; i+4 or i, i+5.

Cyclic peptide analogs of galanin are known in the art. Carpenter et al. (Biochem. 1999, 38, 15295) constructed a cyclized analog of Gal(1-6) which possessed a lactam bridge between the side-chains of Asp4 and Lys8. This resulted in an analog that exhibited low nanomolar receptor binding affinity and a low nanomolar EC50 for the GalR2 receptor subtype.

WO03/099863 discloses a modified galanin peptide sequence that can serve as exemplary precursor for introducing a posttranslational lanthionine ring at position Ser6 and Cys10. Nothing is mentioned about the properties of the resulting cyclic analog.

Green et al. (Bioorg Med Chem. 2013 Jan. 1; 21(1):303-10) used hydrocarbon stapling as a strategy to stabilize the helical conformation of bioactive peptides. Disclosed is a stapled galanin analog wherein Ala-7 and Leu-11 of the full-length galanin was substituted with (S)-2-(4-)pentenyl)alanine. The analog retained agonist activities towards GalR1 and GalR2, and suppressed seizures in a mouse model of epilepsy. No alteration of receptor specificity was observed.

A cyclic galanin-analog of the invention, herein also referred to as "lanthi-galanin", is characterized by a (methyl)lanthioninestructure formed by not more than two of X3, X4, X6, X7, X10, X11 and X13-X19 which together form a (methyl)Lanthionine bridge and wherein said (methyl)Lanthionine bridge is of the size i, i+3 or i, i+4 or i, i+5.

In one embodiment, a galanin analog is of the formula X1-X22, i.e. it contains all of X1 through X22 as defined herein above. In another embodiment, it is a C-terminally truncated variant lacking up to 10 C-terminal residues. For example, it is of the formula X1-X12, lacking all 10 residues X13 through X22. Other truncated variants include X1-X13, X1-X14, X1-X15, X1-X16, X1-X17, X1-X18, X1-X19, X1-X20 and X1-X21. As will be understood by the skilled person, the annotation above refers to an analog including the stretch of contiguous residues e.g. X1-X13 refers to an analog consisting of X1-X2-X3-X4-X5-X6-X7-X8-X9-X10-X11-X12-X13. Variants lacking residues X20-X22 are preferred.

X1 can be selected from pE, G, N, RGRG (SEQ ID NO:2), RGRGN (SEQ ID NO:3) and RGRGG (SEQ ID NO:4). In a preferred aspect, X1 is pE or G, more preferably pE. Introduction of pyroglutamate at position 1 can protect the analog against N-terminal hydrolysis. In addition, it was surprisingly found to shift the biological activity of the analog towards a preference for signaling via the Gal2R. Pyroglutamic acid (also known as PCA, 5-oxoproline, pidolic acid, or pyroglutamate for its basic form) is an uncommon amino acid derivative in which the free amino group of glutamic acid or glutamine cyclizes to form a lactam. It is a metabolite in the glutathione cycle that is converted to glutamate by 5-oxoprolinase. Pyroglutamate is found in many proteins including bacteriorhodopsin. N-terminal glutamic acid and glutamine residues can spontaneously cyclize to become pyroglutamate.

In another embodiment, the lanthi-galanin lacks the N-terminal X1, optionally in combination with a C-terminal truncation of up to 10 residues. Accordingly, also provided is a galanin analog of the formula X2-X22. In a further aspect, the invention provides a variant comprising X2-X12, X2-X13, X2-X14, X2-X15, X2-X16, X2-X17, X2-X18, X2-X19, X2-X20, X2-X21 i.e. containing both an N-terminal and a C-terminal truncation of the general formula X1-X22.

X2 is WN or WT.
Preferably, X2 is WN.
X3 is L, (me)lan, A, D, V, K, Q
X4 is N, T or (me)lan
X5 is S or A
X6 is A or (me)lan
X7 is G, (me)lan, A or K
In one aspect, X3 is L, X4 is N, X5 is A, X6 is A, and/or X7 is G.
X8 is always Y, and X9 is always L
X10 is L, (me)lan or A
X11 is G, A, (me)lan,
X12 is P or A
X13 is H, (me)lan, V, Q, P, E, K, A
X14 is A, (me)lan, L, Q, P, H, K, I
For example, X10 is L, X11 is G, X12 is P, X13 is H, and/or X14 is A.
X15 is V, (me)lan, P, F, G, K, A
X16 is (me)lan, P, F, L or G,
X17 is N, (me)lan, P, G, S, A,
X18 is H, (me)lan, A, L, P, A,
X19 is R, (me)lan, L, M, F, A
X20 is R, A,
X21 is L,
X22 is A, A lanthi-galanin of the invention contains a (methyl) Lanthionine bridge of the size i, i+3 or i, i+4 or i, i+5. Thus, the ring size is limited to those wherein the residues involved in ring formation are spaced by either two, three or four residues. Larger ring sizes were found to be detrimental to the activity. In one embodiment, the (methyl)Lanthionine bridge is of the size i, i+3 or i, i+4. In a specific aspect, the (methyl)Lanthionine bridge is of the size i, i+3. For example, the ring is formed between residues X3 and X6, X4 and X7, X5 and X8, X6 and X9, X7 and X10 or X8 and X11.

Furthermore, it was surprisingly found that ring introduction from position 13 onwards can be done without significant loss of activity while allowing for altered receptor specificity as compared to wildtype galanin. More in particular, introducing a (methyl)lanthionine in the C-terminal half of the peptide was found to give a shift towards GalR2 preference. Accordingly, in one embodiment, two residues selected from the group consisting of X13-X19 together form a (me)Lanthionine bridge. Suitable pairs of residues forming the ring structure include X13 and X16, X13 and X17, X14 and X17, X14 and X18, X15 and X18, and X15 and X19. Exemplary analogs are GalM50, GalM51, GalM52 and GalM75. In a preferred embodiment, residues X20-X22 are absent and two residues selected from the group consisting of X13-X19 together form a (me)Lanthionine bridge.

The C-terminal carboxyl group of a galanin analog according to the invention can be in the free (COOH) or amide ($CONH_2$) form. In one embodiment, the analog is protected by a C-terminal amidation. Depending on its structure, a galanin analog of the invention can have one or more specific biological activitie(s). In one embodiment, the invention provides an analog that is capable of inhibiting cAMP production in cells expressing a galanin R1 receptor (GalR1). Preferably, cAMP production is inhibited with an EC50 of less than 200 nM.

Alternatively, the galanin analog is capable of inducing beta arrestin recruitment in cells expressing GalR1 with an EC50 of less than 400 nM.

The galanin analog is capable of inducing calcium efflux in cells expressing a galanin R2 receptor with an EC50 of less than 100 nM and of inducing beta arrestin recruitment with an EC50 of less than 5 μM.

In a preferred embodiment, the invention provides a cyclic galanin analog having an enhanced capacity to stimulate GalR2 compared to GalR1. The term "GALR2-specific agonist" indicates an analog capable of triggering a response in a cell as a result of the activation of GALR2 by the substance, but which does not activate (or activates with less potency) GALR1 and/or GALR3. Methods of identifying whether or not a compound is an agonist of a galanin receptor are known in the art, for example, Botella et al. (1995) Gastroenterology 108 3-11 and Barblivien et al. (1995) Neuroreport 6 1849-1852. Exemplary GalR2-specific analogs include GalM54 and GalM54tr. The analog may bind to GalR2 with a binding affinity of between 0 and 100 μM and/or it has a specificity of greater than 30-fold for GalR2 over GalR1. Preferably, it has a specificity of greater that 50 fold for GalR2 over GalR1, more preferably, of greater than 100 fold for GalR2 over GalR1. In a specific embodiment, the galanin analog is selected from the group consisting of:

| | |
|---|---|
| GWNmelanNAmelanGYLLGPHAVGNHR | (SEQ ID NO: 6) |
| GWNmelanNAmelanGYLLGPHAVGNH | (SEQ ID NO: 7) |
| GWNLNAAmelanYLmelanGPHAVGNHR | (SEQ ID NO: 8) |
| GWNLNAAmelanYLmelanGPHAVGNH | (SEQ ID NO: 9) |
| GWNLNAAlanYLLlanGPHAVGNHR | (SEQ ID NO: 10) |
| GWNLNAAlanYLLlanGPHAVGNH | (SEQ ID NO: 11) |
| GWNLNAAGYLLGAmelanAVmelanNHR | (SEQ ID NO: 12) |
| GWNLNAAGYLLGAmelanAVmelanNH | (SEQ ID NO: 13) |
| GWNLNAAGYLLGAlanAVlan | (SEQ ID NO: 14) |
| GWNLNAAGYLLGAlanAVlanNHR | (SEQ ID NO: 15) |
| GWNLNAAGYLLGAlanAVlanNH | (SEQ ID NO: 16) |
| GWNLNAAGYLLGAmelanAVGmelanHR | (SEQ ID NO: 17) |
| GWNLNAAGYLLGAlanAVGlan | (SEQ ID NO: 18) |
| GWNLNAAGYLLGAlanAVGlanHR | (SEQ ID NO: 19) |
| GWNLNAAGYLLGAlanAVGNlanR | (SEQ ID NO: 20) |
| GWNLNAAGYLLGAlanAVGNlan | (SEQ ID NO: 21) |
| GWNLNAAGYLLGAlanAVGNHlan | (SEQ ID NO: 22) |
| GWNLNAAGYLLGPHmelanVGmelanHR | (SEQ ID NO: 23) |
| GWNLNAAGYLLGPHlanVGlan | (SEQ ID NO: 24) |
| GWNLNAAGYLLGPHAmelanGNmelanR | (SEQ ID NO: 25) |
| GWNLNAAGYLLGPHAlanGNlan | (SEQ ID NO: 26) |
| GWNLNAAGYLLGASlanVGNHlan | (SEQ ID NO: 27) |
| pEWNLNAAGYLLGAmelanAVmelanNHR | (SEQ ID NO: 28) |
| pEWNLNAAGYLLGAmelanAVGmelanHR | (SEQ ID NO: 29) |
| pEWNLNAAGYLLGAmelanAVmelanNH | (SEQ ID NO: 30) |
| pEWNLNAAGYLLGAlanAVlan | (SEQ ID NO: 31) |

-continued

| | |
|---|---|
| pEWNLNAAlanYLLlan | (SEQ ID NO: 32) |
| pEWNLNAAGYLLGPHmelanVGmelanHR | (SEQ ID NO: 33) |
| GWNLNAAGYLLGmelanHAmelanG | (SEQ ID NO: 34) |
| GWNLNAAGYLLGPmelanAVmelan | (SEQ ID NO: 35) |
| GWNLNAAGYLLAmelanHAmelanG | (SEQ ID NO: 36) |
| GWNLNAAGYLLGAmelanAVmelan | (SEQ ID NO: 37) |
| pEWNLNAAGYLLAmelanHAmelanG | (SEQ ID NO: 38) |
| pEWNLNAAGYLLGAmelanAVmelan | (SEQ ID NO: 39) |
| pEWNLNAAGYLLAlanHAlanG | (SEQ ID NO: 40) |
| pEWNLNAAGYLLAmelanHAmelanGNHR | (SEQ ID NO: 41) |
| GWNLNAAmelanYLmelanGPHAVGNHR | (SEQ ID NO: 8) |
| pEWNLNAAGYLLGPHAmelanGNmelanR | (SEQ ID NO: 42) |
| GWNLNAAGYLLAmelanHAmelanG | (SEQ ID NO: 36) |
| pEWNLNAAGYLLAmelanHAmelanG | (SEQ ID NO: 38) |
| GWNLNAAGYLLGAmelanAVmelan | (SEQ ID NO: 37) |
| pEWNLNAAGYLLGAmelanAVmelan | (SEQ ID NO: 39) |
| GWNVNAAGYLLGAmelanAVmelanNHR | (SEQ ID NO: 43) |
| GWNDNAAGYLLGAmelanAVmelanNHR | (SEQ ID NO: 44) |
| GWNNNAAGYLLGAmelanAVmelanNHR | (SEQ ID NO: 45) |
| GWNLVAAGYLLGAmelanAVmelanNHR | (SEQ ID NO: 46) |
| GWNLKAAGYLLGAmelanAVmelanNHR | (SEQ ID NO: 47) |
| GWNLDAAGYLLGAmelanAVmelanNHR | (SEQ ID NO: 48) |
| GWNLQAAGYLLGAmelanAVmelanNHR | (SEQ ID NO: 49) |
| pEWNLNAAGYLLGPlanAVlan | (SEQ ID NO: 50) |
| pEWTLNAAlanYLLlan | (SEQ ID NO: 51) |
| pEWNLNAAGYLLGPmelanAVmelan | (SEQ ID NO: 52) |
| pEWTLNAAmelanYLLmelan | (SEQ ID NO: 53) |

Specifically preferred analogs include:

| | |
|---|---|
| pEWNLNAAGYLLAmelanHAmelanGNHR (GalM50b), | (SEQ ID NO: 41) |
| GWNLNAAGYLLAmelanHAmelanG (GalM89), | (SEQ ID NO: 36) |
| pEWNLNAAGYLLAmelanHAmelanG (GalM89b), | (SEQ ID NO: 38) |
| pEWNLNAAGYLLGAmelanAVmelanNHR (GalM54), | (SEQ ID NO: 28) |
| pEWNLNAAGYLLGAmelanAVmelanNH (GalM54 tr) | (SEQ ID NO: 30) |
| pEWNLNAAGYLLGPHAmelanGNmelanR (GalM74b) | (SEQ ID NO: 42) |
| pEWNLNAAGYLLGPHmelanVGmelanHR (GalM82) | (SEQ ID NO: 33) |
| pEWNLNAAGYLLGPlanAVlan | (SEQ ID NO: 50) |

| | |
|---|---|
| (4178B isomer B) and | |
| pEWTLNAAlanYLLlan (4179B isomer B) | (SEQ ID NO: 51) |
| pEWNLNAAGYLLGPmelanAVmelan | (SEQ ID NO: 52) |
| pEWTLNAAmelanYLLmelan | (SEQ ID NO: 53) |

In a specific embodiment, the galanin analog is selected from the group consisting of:

| | |
|---|---|
| pEWNLNAAGYLLAmelanHAmelanGNHR (GalM50b), | (SEQ ID NO: 41) |
| GWNLNAAGYLLAmelanHAmelanG (GalM89), | (SEQ ID NO: 36) |
| pEWNLNAAGYLLAmelanHAmelanG (GalM89b), | (SEQ ID NO: 38) |
| pEWNLNAAGYLLGAmelanAVmelanNHR (GalM54), | (SEQ ID NO: 28) |
| pEWNLNAAGYLLGAmelanAVmelanNH (GalM54 tr) | (SEQ ID NO: 30) |
| pEWNLNAAGYLLGPHAmelanGNmelanR (GalM74b) | (SEQ ID NO: 42) |
| pEWNLNAAGYLLGPHmelanVGmelanHR (GalM82) | (SEQ ID NO: 33) |
| pEWNLNAAGYLLGPlanAVlan (4178B isomer B) and | (SEQ ID NO: 50) |
| pEWTLNAAlanYLLlan (4179B isomer B) | (SEQ ID NO: 51) |
| pEWNLNAAGYLLGPmelanAVmelan | (SEQ ID NO: 52) |
| pEWTLNAAmelanYLLmelan | (SEQ ID NO: 53) |

Also provided is a pharmaceutical composition comprising at least one lanthi-galanin according to the invention. A further embodiment relates to a galanin analog according to the invention for use as medicament. A further embodiment relates to a galanin analog selected from the group consisting of:

| | |
|---|---|
| pEWNLNAAGYLLAmelanHAmelanGNHR (GalM50b), | (SEQ ID NO: 41) |
| GWNLNAAGYLLAmelanHAmelanG (GalM89), | (SEQ ID NO: 36) |
| pEWNLNAAGYLLAmelanHAmelanG (GalM89b), | (SEQ ID NO: 38) |
| pEWNLNAAGYLLGAmelanAVmelanNHR (GalM54), | (SEQ ID NO: 28) |
| pEWNLNAAGYLLGAmelanAVmelanNH (GalM54 tr) | (SEQ ID NO: 30) |
| pEWNLNAAGYLLGPHAmelanGNmelanR (GalM74b) | (SEQ ID NO: 42) |
| pEWNLNAAGYLLGPHmelanVGmelanHR (GalM82) | (SEQ ID NO: 33) |
| pEWNLNAAGYLLGPlanAVlan (4178B isomer B) and | (SEQ ID NO: 50) |

-continued

| | |
|---|---|
| pEWTLNAAlanYLLlan (4179B isomer B), for use as medicament. | (SEQ ID NO: 51) |
| pEWNLNAAGYLLGPmelanAVmelan | (SEQ ID NO: 52) |
| pEWTLNAAmelanYLLmelan | (SEQ ID NO: 53) |

Also provided is a pharmaceutical composition comprising a galanin analog selected from the group consisting of:

| | |
|---|---|
| pEWNLNAAGYLLAmelanHAmelanGNHR (GalM50b), | (SEQ ID NO: 41) |
| GWNLNAAGYLLAmelanHAmelanG (GalM89), | (SEQ ID NO: 36) |
| pEWNLNAAGYLLAmelanHAmelanG (GalM89b), | (SEQ ID NO: 38) |
| pEWNLNAAGYLLGAmelanAVmelanNHR (GalM54), | (SEQ ID NO: 28) |
| pEWNLNAAGYLLGAmelanAVmelanNH (GalM54 tr) | (SEQ ID NO: 30) |
| pEWNLNAAGYLLGPHAmelanGNmelanR (GalM74b) | (SEQ ID NO: 42) |
| pEWNLNAAGYLLGPHmelanVGmelanHR (GalM82) | (SEQ ID NO: 33) |
| pEWNLN

```
GWNVAAGYLLGATAVCNHR,       (SEQ ID NO: 94)
GWNDAAGYLLGATAVCNHR,       (SEQ ID NO: 95)
GWNNAAGYLLGATAVCNHR,       (SEQ ID NO: 96)
GWNLVAAGYLLGATAVCNHR,      (SEQ ID NO: 97)
GWNLKAAGYLLGATAVCNHR,      (SEQ ID NO: 98)
GWNLDAAGYLLGATAVCNHR,      (SEQ ID NO: 99)
GWNLQAAGYLLGATAVCNHR,      (SEQ ID NO: 100)
QWNLNAAGYLLGPTAVC,         (SEQ ID NO: 101)
QWTLNAATYLLC,              (SEQ ID NO: 102)
QWNLNAAGYLLGPSAVC,         (SEQ ID NO: 103)
QWTLNAASYLLC               (SEQ ID NO: 104)
```

(ii) inducing dehydration of a Ser or Thr residue of said peptide; and (iii) inducing ring closure by coupling the dehydrated Ser or Thr to the thiol group of the Cys residue of said peptide.

Step (iii) may comprise inducing ring closure by chemical or enzymatic means. Preferably, it comprises enzymatic ring closure. E.g. by exploiting the lanthipeptide enzyme machinery of a (bacterial) host cell according to methods known in the art.

In case the N-terminal residue of the peptide is glutamine (Q), the method preferably further comprises conversion of Q to pE according to methods known in the art, for example as described in Rink et al. (Journal of Pharmacological and Toxicological Methods 61 (2010) 210-218)

Specifically preferred linear peptide sequences for providing a lanthi-galanin include QWNLNAAGYLLATHACGNHR (SEQ ID NO:91) (e.g. to produce GalM50b), GWNLNAAGYLLATHACG (SEQ ID NO:86) (e.g. to produce GalM89), QWNLNAAGYLLATHACG (SEQ ID NO:88) (e.g. to produce GalM89b), QWNLNAAGYLLGATAVCNHR (SEQ ID NO:79) (e.g. to produce GalM54), QWNLNAAGYLLGPHATGNCR (SEQ ID NO:92) (e.g. to produce GalM74b) QWNLNAAGYLLGPHTVGCHR (SEQ ID NO:83) (e.g. to produce GalM82), QWNLNAAGYLLGPSAVC (SEQ ID NO:103) (e.g. to produce 4178B isomer B) and QWTLNAASYLLC (SEQ ID NO:104) (e.g. to produce 4179B isomer B). QWNLNAAGYLLGPTAVC (SEQ ID NO:101) (to produce 4178) QWTLNAATYLLC (SEQ ID NO:102) (to produce 4179)

Also provided is an isolated nucleic acid sequence encoding a precursor peptide recited above, and a vector comprising said nucleic acid sequence, which nucleic acid is genetically fused to a nucleic acid sequence encoding a lanthipeptide-leader sequence.

Preferred nucleic acid sequences are those encoding one of the following peptide sequences:

```
GWNTNACGYLLGPHAVGNHR,      (SEQ ID NO: 58)
GWNTNACGYLLGPHAVGNH,       (SEQ ID NO: 59)
GWNLNAATYLCGPHAVGNHR,      (SEQ ID NO: 60)
GWNLNAATYLCGPHAVGNH        (SEQ ID NO: 61)
GWNLNAASYLLCGPHAVGNHR,     (SEQ ID NO: 62)
GWNLNAASYLLCGPHAVGNH       (SEQ ID NO: 63)
GWNLNAAGYLLGATAVCNHR,      (SEQ ID NO: 64)
GWNLNAAGYLLGATAVCNH,       (SEQ ID NO: 65)
GWNLNAAGYLLGASAVC,         (SEQ ID NO: 66)
GWNLNAAGYLLGASAVCNHR,      (SEQ ID NO: 67)
GWNLNAAGYLLGASAVCNH,       (SEQ ID NO: 68)
GWNLNAAGYLLGATAVGCHR,      (SEQ ID NO: 69)
GWNLNAAGYLLGASAVGC,        (SEQ ID NO: 70)
GWNLNAAGYLLGASAVGCHR,      (SEQ ID NO: 71)
GWNLNAAGYLLGASAVGNCR,      (SEQ ID NO: 72)
GWNLNAAGYLLGASAVGNC,       (SEQ ID NO: 73)
GWNLNAAGYLLGASAVGNHC,      (SEQ ID NO: 74)
GWNLNAAGYLLGPHTVGCHR,      (SEQ ID NO: 75)
GWNLNAAGYLLGPHSVGC,        (SEQ ID NO: 76)
GWNLNAAGYLLGPHATGNCR,      (SEQ ID NO: 77)
GWNLNAAGYLLGPHASGNC,       (SEQ ID NO: 78)
GWNLNAAGYLLGASAVGNHC,      (SEQ ID NO: 74)
QWNLNAAGYLLGATAVCNHR,      (SEQ ID NO: 79)
QWNLNAAGYLLGATAVCNH,       (SEQ ID NO: 80)
QWNLNAAGYLLGASAVC,         (SEQ ID NO: 81)
QWNLNAASYLLC,              (SEQ ID NO: 82)
QWNLNAAGYLLGPHTVGCHR,      (SEQ ID NO: 83)
GWNLNAAGYLLGTHACG,         (SEQ ID NO: 84)
GWNLNAAGYLLGPTAVC,         (SEQ ID NO: 85)
GWNLNAAGYLLATHACG,         (SEQ ID NO: 86)
GWNLNAAGYLLGATAVC,         (SEQ ID NO: 87)
QWNLNAAGYLLATHACG,         (SEQ ID NO: 88)
pEWNLNAAGYLLGATAVC,        (SEQ ID NO: 89)
QWNLNAAGYLLASHACG,         (SEQ ID NO: 90)
QWNLNAAGYLLATHACGNHR,      (SEQ ID NO: 91)
GWNLNAATYLCGPHAVGNHR,      (SEQ ID NO: 60)
QWNLNAAGYLLGPHATGNCR,      (SEQ ID NO: 92)
GWNLNAAGYLLATHACG,         (SEQ ID NO: 86)
QWNLNAAGYLLATHACG,         (SEQ ID NO: 88)
GWNLNAAGYLLGATAVC,         (SEQ ID NO: 87)
QWNLNAAGYLLGATAVC,         (SEQ ID NO: 93)
GWNVAAGYLLGATAVCNHR,       (SEQ ID NO: 94)
GWNDAAGYLLGATAVCNHR,       (SEQ ID NO: 95)
GWNNAAGYLLGATAVCNHR,       (SEQ ID NO: 96)
GWNLVAAGYLLGATAVCNHR,      (SEQ ID NO: 97)
GWNLKAAGYLLGATAVCNHR,      (SEQ ID NO: 98)
```

```
GWNLDAAGYLLGATAVCNHR,    (SEQ ID NO: 99)

GWNLQAAGYLLGATAVCNHR,    (SEQ ID NO: 100)

QWNLNAAGYLLGPTAVC,       (SEQ ID NO: 101)

QWTLNAATYLLC,            (SEQ ID NO: 102)

QWNLNAAGYLLGPSAVC,       (SEQ ID NO: 103)

QWTLNAASYLLC.            (SEQ ID NO: 104)
```

Specifically preferred nucleic acids encoding linear peptide sequences for providing a lanthi-galanin include QWNLNAAGYLLATHACGNHR (SEQ ID NO:91) (e.g. to produce GalM50b), GWNLNAAGYLLATHACG (SEQ ID NO:86) (e.g. to produce GalM89), QWNLNAAGYLLATHACG (SEQ ID NO:88) (e.g. to produce GalM89b), QWNLNAAGYLLGATAVCNHR (SEQ ID NO:79) (e.g. to produce GalM54), QWNLNAAGYLLGPHATGNCR (SEQ ID NO:92) (e.g. to produce GalM74b) QWNLNAAGYLLGPHTVGCHR (SEQ ID NO:83) (e.g. to produce GalM82) QWNLNAAGYLLGPSAVC (SEQ ID NO:103) (e.g. to produce 4178B isomer B) QWTLNAASYLLC (SEQ ID NO:104) (e.g. to produce 4179B isomer B). QWNLNAAGYLLGPTAVC (SEQ ID NO:101) (to produce 4178) and QWTLNAATYLLC (SEQ ID NO:102) (to produce 4179).

Further embodiments relate to a food-grade bacterial host cell, preferably a *L. lactis* host cell, comprising a vector according to the invention, additionally comprising lanthionine-introduction enzymes. For example, the host cell endogenously contains the lantibiotic enzyme machinery, or it is provided with a plasmid encoding the maturation enzymes NisB and NisC, and the translocation enzyme NisT. Such host cells are advantageously used as an oral delivery system for the in situ production of lanthi-galanins in the gut.

Hence, the invention also relates to a pharmaceutical composition comprising viable host cells comprising a nucleic acid sequence encoding a precursor peptide recited above, and a pharmaceutically acceptable carrier, diluent or vehicle. Preferably, the composition is formulated for oral administration.

The host cells capable of producing the lanthi-galanin in situ are suitably used in a method of treating or alleviating the symptoms associated with inflammatory bowel disease, for instance wherein the bowel disease is Crohn's disease or ulcerative colitis (UC).

Therapeutic uses of GalR1 and GalR3 antagonists of the invention are the following. Galanin is thought to play a potentially key role in IBD. Gal1R is the only gal receptor found in colonic tissue. Cloning of the Gal1R gene has revealed multiple recognition sites for the inflammation-associated transcription factor NF kappa B. A GalR1-specific antagonist may result in new pharmacologic therapies for the treatment of diarrhea resulting from the inflammation [Gross 2007 Role of Inflammatory Bowel Disease. Inflamm Bowel Disease 13, 918-32].

Antagonism of GalR3 has been reported to reduce pancreatitis [Barreto S G, 2011 Galanin receptor 3 a potential target for acute pancreatitis therapy. Neurogastroenterol Motil 23(3):e141-51]. GalR3 antagonists seem furthermore to act as antidepressant [Swanson C J, 2005 Anxiolytic- and antidepressant-like profiles of the galanin-3 receptor (Gal3) antagonists SNAP 37889 and SNAP 398299. PNAS 102, 17489-94].

LEGEND TO THE FIGURES

FIG. 1: Exemplary analog GalM51-induced β-arrestin recruitment via GalR1

Figure 2:
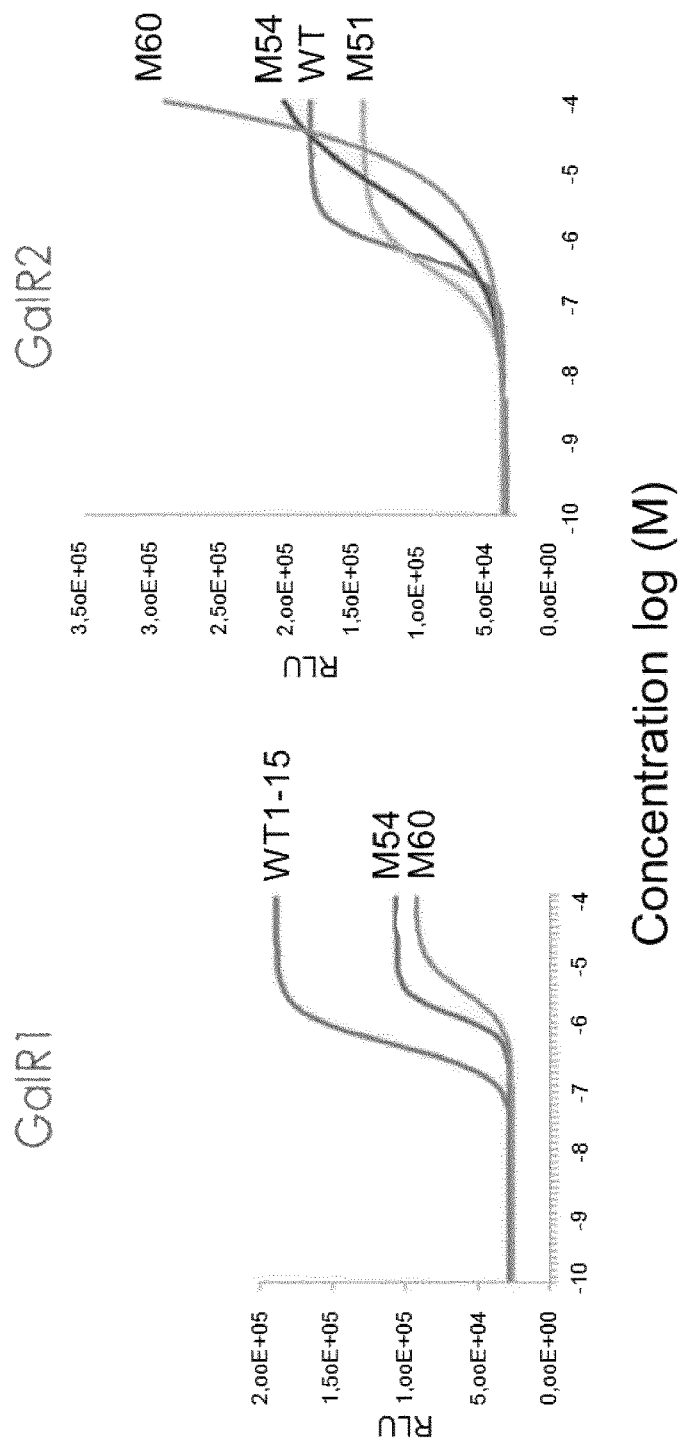

FIG. 2: Exemplary analog GalM54 preferentially stimulates β-arrestin recruitment via GalR2

Figure 3:
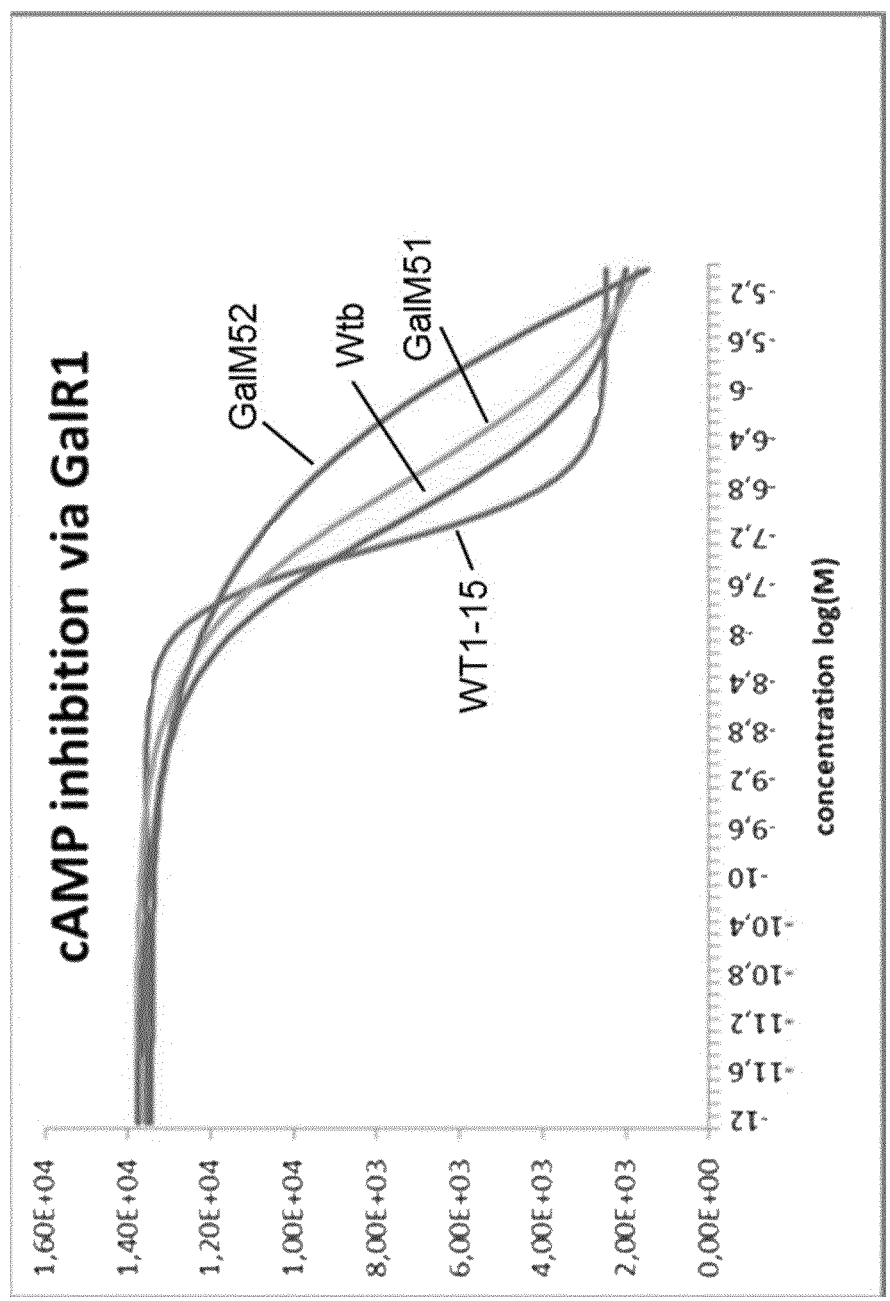

FIG. 3: Exemplary analogs GalM51 and GalM52 inhibit cAMP production via GalR1

EXPERIMENTAL SECTION

Example 1: Synthesis of Lanthionine-Stabilized Galanin Analogs (Lanthi-Galanins)

Lanthionine containing galanin variants were made according to established procedures described for example in Kluskens 2005 Post-translational Modification of Therapeutic Peptides by NisB, the Dehydratase of the Lantibiotic Nisin. Biochemistry 44, 12827-12834; Kluskens 2009 Angiotensin-(1-7) with thioether-bridge: an ACE-resistant, potent Ang-(1-7) analogue. J. Pharmacol. Exper. Ther. 328, 849-854; Rink 2007c NisC, the cyclase of the lantibiotic nisin, can catalyze cyclization of designed non-lantibiotic peptides. Biochemistry 46, 13179-13189.

Briefly, *Lactococcus lactis* comprising a two plasmid system was used. The first plasmid encoded the leader peptide of the lantibiotic nisin MSTKDFNLDLVSVSK-KDSGASPR (SEQ ID NO: 105) genetically fused at its C-terminus to the precursor peptide of the aimed for (methyl)lanthionine-galanin which peptide contains at position [i] a serine/threonine and at position [i+3], [i+4] or [i+5] a cysteine. The plasmid encoding the fusion peptide comprising the nisin leader and the (methyl)lanthionine galanin precursor was co-expressed in *L. lactis* with the second plasmid pIL3BTC plasmid, encoding the maturation enzymes NisB and NisC, and the translocation enzyme NisT. NisB dehydrated the serine or threonine to yield dehydroalanine and dehydrobutyrine, respectively. Subsequently, the cyclase NisC covalently coupled the dehydroamino acid to a cysteine, yielding a lanthionine (lan) or methyllanthionine (melan) respectively. The second plasmid encodes the nisin modification and export enzymes NisBTC.

The practical procedure for production (Kluskens 2005 Post-translational modification of therapeutic peptides by NisB, the dehydratase of the lantibiotic nisin. Biochemistry 44, 12827-34; Rink 2005 Lantibiotic structures as guidelines for the design of peptides that can be modified by lantibiotic enzymes. 44, 8873-82), isolation and purification of the modified galanin variants was as follows:

The culture *Lactococcus lactis* NZ9000 pIL3BTC pNZ-GalM'X' was grown overnight in M17 broth (Difco) supplemented with 0.5% glucose and the antibiotics chloramphenicol (5 µg/ml) and erythromycin (5 µg/ml). Next day 1 ml culture was diluted in 100 ml minimal medium (Jensen P R, Hammer K. 1993 Minimal Requirements for Exponential Growth of *Lactococcus lactis*. Appl Environ Microbiol 59, 4363-6; Rink 2005 Lantibiotic structures as guidelines for the design of peptides that can be modified by lantibiotic enzymes. 44, 8873-82) supplemented with nisin (1 µg/ml). The culture was further grown for 24-48 hours. Peptides from cell-free supernatant were precipitated in 10% trichloroacetic acid (TCA). Subsequently the galanin peptide was liberated from the leader peptide by digestion of the fusion peptide, dissolved in 40 mM Tris (pH=8), 100 mM NaCl, 2 mM CaCl$_2$, with the protease Factor Xa (5 µg) for 18 h at 30° C. The digestion mixture was applied on a Phenomenex C12 250×4.6 mm×4 micron column using a HP1050 HPLC system or a JASCO PU-1580 HPLC system. The peptides were eluted with a gradient using as buffer A (0.1% trifluoracetic acid (TFA) in milliQ) and buffer B (0.1% TFA in acetonitrile). The used gradient was 10% to 50% buffer B with a slope of 1.14%/min. Peaks were collected and dried using a speed-vacuum apparatus. Peptides were analyzed by mass spectrometry after incubation with or without 1-cyano-4-dimethylaminopyridinium tetrafluoroborate (CDAP). An addition of CDAP results in a shift of +25 Dalton and is present when there is no ring closure (Rink. 2007c NisC, the cyclase of the lantibiotic nisin, can catalyze cyclization of designed non-lantibiotic peptides. Biochemistry 46, 13179-13189). When needed, an N-terminal pyroglutamate (pE) was introduced by incubation of the purified galanin peptide containing an N-terminal glutamine for 18 h at 50° C. in 50 mM phosphate buffer (pH=7.6). A second HPLC run was performed for isolation of the galanin variant with the N-terminal pyroglutamate. Quantification of the purified galanin variants was performed by comparing the peak area of the compound in the HPLC chromatogram detected at 280 nm with the area of a known amount of reference Galanine-(1-15). Peptides with a methyllanthionine were enzymatically, D,L stereospecifically cyclized by NisC. Introduction of a lanthionine (lan) into a peptide the stereospecificity has not been established here since, due the reactivity the coupling of the highly reactive dehydroalanine can take place not only via catalysis by NisC but also spontaneously.

Example 2: Activity of Lanthionine-Stabilized Galanin Analogs (Lanthi-Galanins)

The biological activity of the (lanthi)galanins was determined in CHO-K1 cell lines that express either the GalR1, or GalR2 receptor. Activity measurements were performed using commercial kits from DiscoverX for determining arrestin recruitment (GalR1, GalR2) and inhibition of cAMP synthesis (GalR1). In addition, HEK293 cell lines that express the GalR2 receptor have been used for methods from Molecular Probes to measure calcium efflux (GalR2).

TABLE 1

| Galanin | GalR1 | | GalR2 | |
|---|---|---|---|---|
| | Ratio EC50s relative to Gal-(1-15) | | | |
| | β-Arrestin | cAMP | β-Arrestin | $Ca^{2+}$ |
| GWNLNAAGYLLGPHAVGNHRSFSDKNGLTS (SEQ ID NO: 106) Wild type galanine-(1-30) Bersani 1991 FEBS Letters 283, 189-194 | ND | ND | ND | ND |
| Lanthi-galanin precursors. T . . . C and S . . . C have been enzymatically converted into methyllanthionine (melan) and lanthionine (lan), purified and activites measured | | | | |
| Gal1-15: GWTLNSAGYLLGPHA (SEQ ID NO: 107) Diaz-Cabiale 2005 Neuropeptides 39, 185-190 | 1 | 1 | 1 | 1 |
| T3N-Gal-(1-22); termed: GalWtb GWNLNAAGYLLGPHAVGNHR (SEQ ID NO: 108) | 1.7 | 1.6 | 3.8 | 2.3 |
| GalM50: GWNLNAAGYLLATHACGNHR (SEQ ID NO: 109) | 3.8 | 14 | 0.5 | 2.8 |
| GalM50b: pEWNLNAAGYLLATHACGNHR (SEQ ID NO: 110) | ND | no activity | 6.7 | 4.8 |
| GalM51: GWNLNAAGYLLGATAVCNHR (SEQ ID NO: 64) | 1.5 | 3.6 | 0.6 | 2.9 |
| GalM52: GWNLNAAGYLLGPHTVGCHR (SEQ ID NO: 75) | 8.3 | 7.5 | 0.6 | 1.9 |
| GalM54: pEWNLNAAGYLLGATAVCNHR (SEQ ID NO: 111) | >1000 | >1000 | 1.4 | 3.4 |
| GalM54tr: pEWNLNAAGYLLGATAVCNH (SEQ ID NO: 112) | >1000 | 16 | 1 | 1.2 |
| GalM60: GWNLNAATYLCGPHAVGNHR (SEQ ID NO: 60) | 12.7 | >1000 | >1000 | 8.7 |
| GalM73: GWNLNAASYLLCGPHAVGNHR (SEQ ID NO: 62) | 21.2 | no activity | 45 | 5.0 |

TABLE 1-continued

| Galanin | GalR1 | | GalR2 | |
|---|---|---|---|---|
| | Ratio EC50s relative to Gal-(1-15) | | | |
| | β-Arrestin | cAMP | β-Arrestin | Ca$^{2+}$ |
| GalM74: GWNLNAAGYLLGPHATGNCR (SEQ ID NO: 77) | 2.3 | 4.4 | 2.6 | 5.0 |
| GalM74b: pEWNLNAAGYLLGPHATGNCR (SEQ ID NO: 113) | 129 | No activity | 4.2 | 2.6 |
| GalM75: GWNLNAAGYLLGASAVCNHR (SEQ ID NO: 67) | 4.3 | 1.6 | 1.8 | 3 |
| GalM76: GWNLNAAGYLLGATAVGCHR (SEQ ID NO: 69) | 1 | 0.6 | 1.0 | 0.9 |
| GalM76b: pEWNLNAAGYLLGATAVGCHR (SEQ ID NO: 114) | 9.6 | 12.2 | 0.5 | 1 |
| GalM77: GWNLNAAGYLLGASAVGCHR (SEQ ID NO: 71) | 1.6 | 2 | 3.8 | 2.6 |
| GalM78: GWNLNAAGYLLGASAVGNCR (SEQ ID NO: 72) | 1.6 | 1.6 | 2.7 | 2.1 |
| GalM79: GWNLNAAGYLLGASAVGNHC (SEQ ID NO: 74) | 1.6 | ND | 0.7 | 1.9 |
| GalM82: pEWNLNAASYLLC (SEQ ID NO: 115) | ND | ND | 493 | 12.9 |
| GalM83: pEWNLNAAGYLLGPHTVGCHR (SEQ ID NO: 116) | 123 | no activity | 78 | 7.3 |
| GalM84: GWNLNAAGYLLGTHACG (SEQ ID NO: 84) | 35 | ND | >1000 | 6.3 |
| GalM85: GWNLNAAGYLLGPTAVC (SEQ ID NO: 85) | 18 | 11.6 | 6.2 | 4.7 |
| GalM87: pEWNLNAAGYLLGPTAVC (SEQ ID NO: 117) | 260 | no activity | 4.8 | 3 |
| GalM89: GWNLNAAGYLLATHACG (SEQ ID NO: 86) | 148 | no activity | 3 | 2.6 |
| GalM89b: pEWNLNAAGYLLATHACG (SEQ ID NO: 118) | no activity | no activity | 2.7 | 2.1 |
| GalM90: GWNLNAAGYLLGATAVC (SEQ ID NO: 87) | 2.7 | 4.9 | 3.2 | 4.6 |
| GalM91: pEWNLNAAGYLLGATAVC (SEQ ID NO: 89) | 3 | >1000 | 1.5 | 1.3 |
| GalM92: GWNVNAAGYLLGATAVCNHR (SEQ ID NO: 94) | 10.1 | ND | 3.3 | 4.4 |
| GalM93: GWNDNAAGYLLGATAVCNHR (SEQ ID NO: 95) | 34.6 | ND | 141 | 7.2 |
| GalM94: GWNNNAAGYLLGATAVCNHR (SEQ ID NO: 96) | 70.3 | ND | ND | 7.1 |
| GalM95: GWNLVAAGYLLGATAVCNHR (SEQ ID NO: 97) | ND | ND | ND | 107 |
| GalM96: GWNLKAAGYLLGATAVCNHR (SEQ ID NO: 98) | ND | ND | ND | 534 |
| GalM97: GWNLDAAGYLLGATAVCNHR (SEQ ID NO: 99) | ND | ND | ND | 502 |
| GalM98: GWNLQAAGYLLGATAVCNHR (SEQ ID NO: 100) | ND | ND | ND | 6.7 |

TABLE 1-continued

| Galanin | GalR1 β-Arrestin | GalR1 cAMP | GalR2 β-Arrestin | GalR2 Ca²⁺ |
|---|---|---|---|---|
| | Ratio EC50s relative to Gal-(1-15) | | | |
| GalWtb: GWNLNAAGYLLGPHAVGNHR (SEQ ID NO: 108) | 1.7 | 1.6 | 3.8 | 2.7 |
| GalM92: GWNVNAAGYLLGATAVCNHR (SEQ ID NO: 94) | 5.3 | 6.1 | 1.8 | 4.4 |
| GalM93: GWNDNAAGYLLGATAVCNHR (SEQ ID NO: 95) | 30 | 41 | 141 | 7.2 |
| GalM94: GWNNNAAGYLLGATAVCNHR (SEQ ID NO: 96) | 46 | 41 | 5.4 | 7.1 |
| GalM95: GWNLVAAGYLLGATAVCNHR (SEQ ID NO: 97) | no activity | no activity | >1000 | 107 |
| GalM96: GWNLKAAGYLLGATAVCNHR (SEQ ID NO: 98) | NA | no activity | no activity | 534 |
| GalM97: GWNLDAAGYLLGATAVCNHR (SEQ ID NO: 99) | no activity | no activity | >1000 | 502 |
| GalM98: GWNLQAAGYLLGATAVCNHR (SEQ ID NO: 100) | 23 | 28 | 53 | 6.7 |
| GalM101: GWNLNKAGYLLGPHAVGNHR (SEQ ID NO: 119) | 365 | no activity | no activity | 118 |
| GalM102: GWNLNDAGYLLGPHAVGNHR (SEQ ID NO: 120) | NA | no activity | no activity | no activity |
| GalM103: GWNLNLAGYLLGPHAVGNHR (SEQ ID NO: 121) | >1000 | 14.1 | no activity | no activity |
| GalM104: GWNLNWAGYLLGPHAVGNHR (SEQ ID NO: 122) | NA | NA | NA | NA |
| GalM105: GWNLNAAKYLLGPHAVGNHR (SEQ ID NO: 123) | no activity | no activity | 29 | 45 |
| GalM106: GWNLNAADYLLGPHAVGNHR (SEQ ID NO: 124) | NA | no activity | no activity | no activity |
| GalM107: GWNLNAAQYLLGPHAVGNHR (SEQ ID NO: 125) | no activity | no activity | >1000 | 31 |
| GalM108: GWNLNAAPYLLGPHAVGNHR (SEQ ID NO: 126) | NA | no activity | >1000 | no activity |

Results

The results are summarized in Table 1. Values indicate the EC50 of the analog expressed relative to that observed for linear galanin(1-15), which is set at a value of 1.0. ND indicates 'not determined'.

It was surprisingly found that introduction of a (methyl) lanthionine in the C-terminus of the galanin peptide gives a slight shift towards GalR2 preference. Especially GalM50b, GalM89b, GalM54, GalM87, GalM74b have a preference for stimulating GalR2. The presence of an N-terminal pE seems to contribute to the preference for GalR2 of some analogs (e.g. GalM50b, GalM89b, GalM74b), but not of others (e.g. GalM76b).

Furthermore, a preferred ring position with respect to activity appears to be at the C-terminal part. Preferably, the ring is positioned after X12. GalM73, despite having the ring more central, has retained some activity. GalM82 is of particular interest because, despite its low activity, it is small and hydrophobic which most likely favors passage over the blood brain barrier (BBB). Moreover, both the N-terminus and C-terminus are protected, and it can be easily synthesized chemically.

In addition GalM92 and GalM94 which have a L4V and L4N substitution, respectively, have comparable efficacy via GalR2 like GalWtb.

Example 3

Chemically Synthesized Lanthionine Analogs of Galanine Obtained by Base Assisted Sulfur Extrusion of Disulfide Bridge Variants:

Two peptides were ordered at Pepscan as crude material:
1) Sym-4178: H-QWNLNAAGYLLGPcAVC-OH (SEQ ID NO:127)

This peptide is related to GalM87. However, while the biologically synthesized GalM87 likely is D,L lanthionine containing, the chemical synthesis leads to more than one isomer. Interestingly one of the lanthionine-containing isomers 4178B (Table 2) is highly active.

2) Sym-4179: H-QWTLNAAcYLLC-OH (SEQ ID NO:128).

This peptide is related to GalM82 (Table 1). However, while the biologically synthesized GalM82 likely is D,L lanthionine containing, the chemical synthesis leads to more than one isomer. Most interestingly one of these, 4179B (Table 2) seems to have high activity.

Peptide was dissolved in 0.3% ammonia. Peptides were incubated o/n at 37° C. for the introduction of the lanthionine via base assisted sulfur extrusion of the disulfide bridged peptide. Different isomers could be isolated by HPLC applying the same method as was used as for the biologically produced peptides. Different isomers were purified and lyophilized. Dry peptides were dissolved in 100 mM phosphate buffer pH=7.6 and peptides were incubated o/n at 50° C. After HPLC purification peptides with a pE formation were selected and used in the different Galanin receptor activation assays.

Results:

TABLE 2

| Lanthi-galanin variants | | Ratio EC50s relative to Gal-(1-15) | | | |
|---|---|---|---|---|---|
| | | GalR1 | | GalR2 | |
| chemically obtained by base-assisted sulfur extrusion | | β-Arrestin | cAMP inhibition | β-Arrestin | Ca efflux |
| 4178 | similar to M87 but possibly a different lanthioninen | | | | |
| 4178 A | pEWNLNAAGYLLGPlanAVlan (SEQ ID NO: 50) isomer A | >1000 | no activity | 137 | 11 |
| 4178 B | pEWNLNAAGYLLGPlanAVlan (SEQ ID NO: 50) isomer B | 39 | no activity | 2.3 | 1.4 |
| 4179 | similar to M82 but likely a different lanthionine isomer | | | | |
| 4179 A | pEWTLNAAlanYLLlan (SEQ ID NO: 51) isomer A | no activity | no activity | NA | 94 |
| 4179 B | pEWTLNAAlanYLLlan (SEQ ID NO: 51) isomer B | 720 | no activity | 3.8 | 2.6 |
| 4179 C | pEWTLNAAlanYLLlan (SEQ ID NO: 51) isomer C | ND | ND | ND | 248 |

Isomers A, B, C are the different unidentified isomers which could be isolated after the thioether introduction; ND / not determined. Lan . . . lan is 1 lanthionine (Ala-S-Ala).

The invention claimed is:
1. Galanin analog selected from the group consisting of:

```
GWNmelanNAmelanGYLLGPHAVGNHR,      (SEQ ID NO: 6)
GWNmelanNAmelanGYLLGPHAVGNH,       (SEQ ID NO: 7)
GWNLNAAmelanYLmelanGPHAVGNHR,      (SEQ ID NO: 8)
GWNLNAAmelanYLmelanGPHAVGNH,       (SEQ ID NO: 9)
GWNLNAAlanYLLlanGPHAVGNHR,         (SEQ ID NO: 10)
GWNLNAAlanYLLlanGPHAVGNH,          (SEQ ID NO: 11)
GWNLNAAGYLLGAmelanAVmelanNHR,      (SEQ ID NO: 12)
GWNLNAAGYLLGAmelanAVmelanNH,       (SEQ ID NO: 13)
GWNLNAAGYLLGAlanAVlan,             (SEQ ID NO: 14)
GWNLNAAGYLLGAlanAVlanNHR,          (SEQ ID NO: 15)
GWNLNAAGYLLGAlanAVlanNH,           (SEQ ID NO: 16)
GWNLNAAGYLLGAmelanAVGmelanHR,      (SEQ ID NO: 17)
GWNLNAAGYLLGAlanAVGlan,            (SEQ ID NO: 18)
GWNLNAAGYLLGAlanAVGlanHR,          (SEQ ID NO: 19)
GWNLNAAGYLLGAlanAVGNlanR,          (SEQ ID NO: 20)
GWNLNAAGYLLGAlanAVGNlan,           (SEQ ID NO: 21)
GWNLNAAGYLLGAlanAVGNHlan,          (SEQ ID NO: 22)
```

-continued

| | |
|---|---|
| GWNLNAAGYLLGPHmelanVGmelanHR, | (SEQ ID NO: 23) |
| GWNLNAAGYLLGPHlanVGlan, | (SEQ ID NO: 24) |
| GWNLNAAGYLLGPHAmelanGNmelanR, | (SEQ ID NO: 25) |
| GWNLNAAGYLLGPHAlanGNlan, | (SEQ ID NO: 26) |
| GWNLNAAGYLLGASlanVGNHlan, | (SEQ ID NO: 27) |
| pEWNLNAAGYLLGAmelanAVmelanNHR, | (SEQ ID NO: 28) |
| pEWNLNAAGYLLGAmelanAVGmelanHR, | (SEQ ID NO: 29) |
| pEWNLNAAGYLLGAmelanAVmelanNH, | (SEQ ID NO: 30) |
| pEWNLNAAGYLLGAlanAVlan, | (SEQ ID NO: 31) |
| pEWNLNAAlanYLLlan, | (SEQ ID NO: 32) |
| pEWNLNAAGYLLGPHmelanVGmelanHR, | (SEQ ID NO: 33) |
| GWNLNAAGYLLGmelanHAmelanG, | (SEQ ID NO: 34) |
| GWNLNAAGYLLGPmelanAVmelan, | (SEQ ID NO: 35) |
| GWNLNAAGYLLAmelanHAmelanG, | (SEQ ID NO: 36) |
| GWNLNAAGYLLGAmelanAVmelan, | (SEQ ID NO: 37) |
| pEWNLNAAGYLLAmelanHAmelanG, | (SEQ ID NO: 38) |
| pEWNLNAAGYLLGAmelanAVmelan, | (SEQ ID NO: 39) |
| pEWNLNAAGYLLAlanHAlanG, | (SEQ ID NO: 40) |
| pEWNLNAAGYLLAmelanHAmelanGNHR, | (SEQ ID NO: 41) |
| GWNLNAAmelanYLmelanGPHAVGNHR, | (SEQ ID NO: 8) |
| pEWNLNAAGYLLGPHAmelanGNmelanR, | (SEQ ID NO: 42) |
| GWNLNAAGYLLAmelanHAmelanG, | (SEQ ID NO: 36) |
| pEWNLNAAGYLLAmelanHAmelanG, | (SEQ ID NO: 38) |
| GWNLNAAGYLLGAmelanAVmelan, | (SEQ ID NO: 37) |
| pEWNLNAAGYLLGAmelanAVmelan, | (SEQ ID NO: 39) |
| GWNVNAAGYLLGAmelanAVmelanNHR, | (SEQ ID NO: 43) |
| GWNDNAAGYLLGAmelanAVmelanNHR, | (SEQ ID NO: 44) |
| GWNNNAAGYLLGAmelanAVmelanNHR, | (SEQ ID NO: 45) |
| GWNLVAAGYLLGAmelanAVmelanNHR, | (SEQ ID NO: 46) |
| GWNLKAAGYLLGAmelanAVmelanNHR, | (SEQ ID NO: 47) |
| GWNLDAAGYLLGAmelanAVmelanNHR, | (SEQ ID NO: 48) |
| GWNLQAAGYLLGAmelanAVmelanNHR, | (SEQ ID NO: 49) |
| pEWNLNAAGYLLGPlanAVlan, | (SEQ ID NO: 50) |
| pEWTLNAAlanYLLlan, | (SEQ ID NO: 51) |
| pEWNLNAAGYLLGPmelanAVmelan, or | (SEQ ID NO: 52) |
| pEWTLNAAmelanYLLmelan. | (SEQ ID NO: 53) |

2. A pharmaceutical composition comprising at least one galanin analog according to claim 1.

3. A method for treatment of Multiple Sclerosis, Alzheimer's disease, anxiety, depression, convulsions and brain injury, in a subject, said method comprising administering to the subject the pharmaceutical composition of claim 2.

4. A method for providing a cyclic galanin analog according to claim 1, comprising the steps of
(i) providing a peptide selected from the group consisting of

| | |
|---|---|
| GWNTNACGYLLGPHAVGNHR, | (SEQ ID NO: 58) |
| GWNTNACGYLLGPHAVGNH, | (SEQ ID NO: 59) |
| GWNLNAATYLCGPHAVGNHR, | (SEQ ID NO: 60) |
| GWNLNAATYLCGPHAVGNH, | (SEQ ID NO: 61) |
| GWNLNAASYLLCGPHAVGNHR, | (SEQ ID NO: 62) |
| GWNLNAASYLLCGPHAVGNH, | (SEQ ID NO: 63) |
| GWNLNAAGYLLGATAVCNHR, | (SEQ ID NO: 64) |
| GWNLNAAGYLLGATAVCNH, | (SEQ ID NO: 65) |
| GWNLNAAGYLLGASAVC, | (SEQ ID NO: 66) |
| GWNLNAAGYLLGASAVCNHR, | (SEQ ID NO: 67) |
| GWNLNAAGYLLGASAVCNH, | (SEQ ID NO: 68) |
| GWNLNAAGYLLGATAVGCHR, | (SEQ ID NO: 69) |
| GWNLNAAGYLLGASAVGC, | (SEQ ID NO: 70) |
| GWNLNAAGYLLGASAVGCHR, | (SEQ ID NO: 71) |
| GWNLNAAGYLLGASAVGNCR, | (SEQ ID NO: 72) |
| GWNLNAAGYLLGASAVGNC, | (SEQ ID NO: 73) |
| GWNLNAAGYLLGASAVGNHC, | (SEQ ID NO: 74) |
| GWNLNAAGYLLGPHTVGCHR, | (SEQ ID NO: 75) |
| GWNLNAAGYLLGPHSVGC, | (SEQ ID NO: 76) |
| GWNLNAAGYLLGPHATGNCR, | (SEQ ID NO: 77) |
| GWNLNAAGYLLGPHASGNC, | (SEQ ID NO: 78) |
| GWNLNAAGYLLGASAVGNHC, | (SEQ ID NO: 74) |
| QWNLNAAGYLLGATAVCNHR, | (SEQ ID NO: 79) |
| QWNLNAAGYLLGATAVCNH, | (SEQ ID NO: 80) |
| QWNLNAAGYLLGASAVC, | (SEQ ID NO: 81) |
| QWNLNAASYLLC, | (SEQ ID NO: 82) |
| QWNLNAAGYLLGPHTVGCHR, | (SEQ ID NO: 83) |
| GWNLNAAGYLLGTHACG, | (SEQ ID NO: 84) |
| GWNLNAAGYLLGPTAVC, | (SEQ ID NO: 85) |
| GWNLNAAGYLLATHACG, | (SEQ ID NO: 86) |
| GWNLNAAGYLLGATAVC, | (SEQ ID NO: 87) |
| QWNLNAAGYLLATHACG, | (SEQ ID NO: 88) |
| QWNLNAAGYLLGATAVC, | (SEQ ID NO: 93) |
| QWNLNAAGYLLASHACG, | (SEQ ID NO: 90) |
| QWNLNAAGYLLATHACGNHR, | (SEQ ID NO: 91) |
| GWNLNAATYLCGPHAVGNHR, | (SEQ ID NO: 60) |
| QWNLNAAGYLLGPHATGNCR, | (SEQ ID NO: 92) |
| GWNLNAAGYLLATHACG, | (SEQ ID NO: 86) |

-continued

| | |
|---|---|
| QWNLNAAGYLLATHACG, | (SEQ ID NO: 88) |
| GWNLNAAGYLLGATAVC, | (SEQ ID NO: 87) |
| QWNLNAAGYLLGATAVC, | (SEQ ID NO: 93) |
| GWNVNAAGYLLGATAVCNHR, | (SEQ ID NO: 94) |
| GWNDNAAGYLLGATAVCNHR, | (SEQ ID NO: 95) |
| GWNNNAAGYLLGATAVCNHR, | (SEQ ID NO: 96) |
| GWNLVAAGYLLGATAVCNHR, | (SEQ ID NO: 97) |
| GWNLKAAGYLLGATAVCNHR, | (SEQ ID NO: 98) |
| GWNLDAAGYLLGATAVCNHR, | (SEQ ID NO: 99) |
| GWNLQAAGYLLGATAVCNHR, | (SEQ ID NO: 100) |
| QWNLNAAGYLLGPSAVC, | (SEQ ID NO: 103) |
| QWTLNAASYLLC, | (SEQ ID NO: 104) |
| QWNLNAAGYLLGPTAVC, and | (SEQ ID NO: 101) |
| QWTLNAATYLLC. | (SEQ ID NO: 102) |

(ii) inducing dehydration of a Ser or Thr residue of said peptide;
(iii) inducing ring closure by coupling the dehydrated Ser or Thr to the thiol group of the Cys residue of said peptide; and
(iv) converting the N-terminal Q to pE.

5. Method according to claim 4, wherein step (iii) comprises inducing ring closure by chemical or enzymatic means.

* * * * *

SEQUENCE LISTING

```
<160> NUMBER OF SEQ ID NOS: 128

<210> SEQ ID NO 1
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(5)
<223> OTHER INFORMATION: /replace="pyroGlu" or "Gly" or "Asn" or
      "Arg-Gly-Arg-Gly" or "Arg-Gly-Arg-Gly-Gly"
<220> FEATURE:
<221> NAME/KEY: MISC_FEATURE
<222> LOCATION: (1)..(5)
<223> OTHER INFORMATION: /note="This region may encompass 1-5 residues"
<220> FEATURE:
<221> NAME/KEY: VARIANT
<222> LOCATION: (7)..(7)
<223> OTHER INFORMATION: /replace"Thr"
<220> FEATURE:
```

```
<221> NAME/KEY: VARIANT
<222> LOCATION: (8)..(8)
<223> OTHER INFORMATION: /replace="Abu" or "Ala" or "Asp" or "Val" or
      "Lys" or "Gln" or "Asn"
<220> FEATURE:
<221> NAME/KEY: VARIANT
<222> LOCATION: (9)..(9)
<223> OTHER INFORMATION: /replace="Thr" or "Gln" or "Abu" or "Ala"
<220> FEATURE:
<221> NAME/KEY: VARIANT
<222> LOCATION: (10)..(10)
<223> OTHER INFORMATION: /replace="Ala"
<220> FEATURE:
<221> NAME/KEY: VARIANT
<222> LOCATION: (11)..(11)
<223> OTHER INFORMATION: /replace="Abu"
<220> FEATURE:
<221> NAME/KEY: VARIANT
<222> LOCATION: (12)..(12)
<223> OTHER INFORMATION: /replace="Abu" or "Ala" or "Lys"
<220> FEATURE:
<221> NAME/KEY: VARIANT
<222> LOCATION: (15)..(15)
<223> OTHER INFORMATION: /replace="Abu" or "Ala"
<220> FEATURE:
<221> NAME/KEY: VARIANT
<222> LOCATION: (16)..(16)
<223> OTHER INFORMATION: /replace="Ala" or "Abu"
<220> FEATURE:
<221> NAME/KEY: VARIANT
<222> LOCATION: (17)..(17)
<223> OTHER INFORMATION: /replace="Ala" or "Abu"
<220> FEATURE:
<221> NAME/KEY: VARIANT
<222> LOCATION: (18)..(18)
<223> OTHER INFORMATION: /replace="Abu" or "Val" or "Gln" or "Pro" or
      "Glu" or "Lys" or "Ala"
<220> FEATURE:
<221> NAME/KEY: VARIANT
<222> LOCATION: (19)..(19)
<223> OTHER INFORMATION: /replace="Abu" or "Leu" or "Gln" or "Pro" or
      "His" or "Lys" or "Ile"
<220> FEATURE:
<221> NAME/KEY: VARIANT
<222> LOCATION: (20)..(20)
<223> OTHER INFORMATION: /replace="Abu" or "Pro" or "Phe" or "Gly" or
      "Lys" or "Ala"
<220> FEATURE:
<221> NAME/KEY: VARIANT
<222> LOCATION: (21)..(21)
<223> OTHER INFORMATION: /replace="Abu" or "Phe" or "Leu" or "Asn" or
      "Gly" or "Ala"
<220> FEATURE:
<221> NAME/KEY: VARIANT
<222> LOCATION: (22)..(22)
<223> OTHER INFORMATION: /replace="Abu" or "Pro" or "Gly" or "Ser" or
      "Ala" or "His"
<220> FEATURE:
<221> NAME/KEY: VARIANT
<222> LOCATION: (23)..(23)
<223> OTHER INFORMATION: /replace="Abu" or "Ala" or "Leu" or "Pro" or
      "Arg"
<220> FEATURE:
<221> NAME/KEY: VARIANT
<222> LOCATION: (24)..(24)
<223> OTHER INFORMATION: /replace="Abu" or "Leu" or "Met" or "Phe" or
      "Ala"
<220> FEATURE:
<221> NAME/KEY: VARIANT
<222> LOCATION: (25)..(25)
<223> OTHER INFORMATION: /replace="Ala"
<220> FEATURE:
<221> NAME/KEY: MISC_FEATURE
<222> LOCATION: (1)..(27)
<223> OTHER INFORMATION: /note="Positions 8, 9, 11, 12 and 15-24 may
      encompass a single methylLanthionine or Lanthionine bridge of the
      structure Abu-S-Ala, Ala-S-Abu or Ala-S-Ala"
<220> FEATURE:
<221> NAME/KEY: MISC_FEATURE
```

```
<222> LOCATION: (1)..(27)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 1

Arg Gly Arg Gly Asn Trp Asn Leu Asn Ser Ala Gly Tyr Leu Leu Gly
1               5                   10                  15

Pro His Ala Val Pro Asn His Arg Arg Leu Ala
            20                  25

<210> SEQ ID NO 2
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Arg Gly Arg Gly
1

<210> SEQ ID NO 3
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Arg Gly Arg Gly Asn
1               5

<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Arg Gly Arg Gly Gly
1               5

<210> SEQ ID NO 5
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(5)
<223> OTHER INFORMATION: /replace="pyroGlu" or "Gly" or "Asn" or
      "Arg-Gly-Arg-Gly" or "Arg-Gly-Arg-Gly-Gly"
<220> FEATURE:
<221> NAME/KEY: MISC_FEATURE
<222> LOCATION: (1)..(5)
```

```
<223> OTHER INFORMATION: /note="This region may encompass 1-5 residues"
<220> FEATURE:
<221> NAME/KEY: VARIANT
<222> LOCATION: (7)..(7)
<223> OTHER INFORMATION: /replace="Thr"
<220> FEATURE:
<221> NAME/KEY: VARIANT
<222> LOCATION: (8)..(8)
<223> OTHER INFORMATION: /replace="Abu" or "Ala" or "Asp" or "Val" or
      "Lys" or "Gln"
<220> FEATURE:
<221> NAME/KEY: VARIANT
<222> LOCATION: (9)..(9)
<223> OTHER INFORMATION: /replace="Thr" or "Abu" or "Ala"
<220> FEATURE:
<221> NAME/KEY: VARIANT
<222> LOCATION: (10)..(10)
<223> OTHER INFORMATION: /replace="Ala"
<220> FEATURE:
<221> NAME/KEY: VARIANT
<222> LOCATION: (11)..(11)
<223> OTHER INFORMATION: /replace="Abu"
<220> FEATURE:
<221> NAME/KEY: VARIANT
<222> LOCATION: (12)..(12)
<223> OTHER INFORMATION: /replace="Abu" or "Ala" or "Lys"
<220> FEATURE:
<221> NAME/KEY: VARIANT
<222> LOCATION: (15)..(15)
<223> OTHER INFORMATION: /replace="Abu" or "Ala"
<220> FEATURE:
<221> NAME/KEY: VARIANT
<222> LOCATION: (16)..(16)
<223> OTHER INFORMATION: /replace="Ala" or "Abu"
<220> FEATURE:
<221> NAME/KEY: VARIANT
<222> LOCATION: (17)..(17)
<223> OTHER INFORMATION: /replace="Ala"
<220> FEATURE:
<221> NAME/KEY: VARIANT
<222> LOCATION: (18)..(18)
<223> OTHER INFORMATION: /replace="Abu" or "Val" or "Gln" or "Pro" or
      "Glu" or "Lys" or "Ala"
<220> FEATURE:
<221> NAME/KEY: VARIANT
<222> LOCATION: (19)..(19)
<223> OTHER INFORMATION: /replace="Abu" or "Leu" or "Gln" or "Pro" or
      "His" or "Lys" or "Ile"
<220> FEATURE:
<221> NAME/KEY: VARIANT
<222> LOCATION: (20)..(20)
<223> OTHER INFORMATION: /replace="Abu" or "Pro" or "Phe" or "Gly" or
      "Lys" or "Ala"
<220> FEATURE:
<221> NAME/KEY: VARIANT
<222> LOCATION: (21)..(21)
<223> OTHER INFORMATION: /replace="Abu" or "Phe" or "Leu" or "Gly" or
      "Ala"
<220> FEATURE:
<221> NAME/KEY: VARIANT
<222> LOCATION: (22)..(22)
<223> OTHER INFORMATION: /replace="Abu" or "Pro" or "Gly" or "Ser" or
      "Ala"
<220> FEATURE:
<221> NAME/KEY: VARIANT
<222> LOCATION: (23)..(23)
<223> OTHER INFORMATION: /replace="Abu" or "Ala" or "Leu" or "Pro"
<220> FEATURE:
<221> NAME/KEY: VARIANT
<222> LOCATION: (24)..(24)
<223> OTHER INFORMATION: /replace="Abu" or "Leu" or "Met" or "Phe" or
      "Ala"
<220> FEATURE:
<221> NAME/KEY: VARIANT
<222> LOCATION: (25)..(25)
<223> OTHER INFORMATION: /replace="Ala"
<220> FEATURE:
<221> NAME/KEY: MISC_FEATURE
<222> LOCATION: (1)..(27)
```

```
<223> OTHER INFORMATION: /note="Positions 8, 9, 11, 12, 15, 16 and 18-24
      may encompass a single methylLanthionine or Lanthionine bridge of
      the structure Abu-S-Ala, Ala-S-Abu or Ala-S-Ala"
<220> FEATURE:
<221> NAME/KEY: MISC_FEATURE
<222> LOCATION: (1)..(27)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 5

Arg Gly Arg Gly Asn Trp Asn Leu Asn Ser Ala Gly Tyr Leu Leu Gly
1               5                   10                  15

Pro His Ala Val Pro Asn His Arg Arg Leu Ala
            20                  25

<210> SEQ ID NO 6
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4),(7)
<223> OTHER INFORMATION: Xaa = methylLanthionine.  A single
      methylLanthionine residue represents Abu-S-Ala or Ala-S-Abu and is
      incorporated into the peptide chain at positions 4 and 7

<400> SEQUENCE: 6

Gly Trp Asn Xaa Asn Ala Xaa Gly Tyr Leu Leu Gly Pro His Ala Val
1               5                   10                  15

Gly Asn His Arg
            20

<210> SEQ ID NO 7
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4),(7)
<223> OTHER INFORMATION: Xaa = methylLanthionine.  A single
      methylLanthionine residue represents Abu-S-Ala or Ala-S-Abu and is
      incorporated into the peptide chain at positions 4 and 7

<400> SEQUENCE: 7

Gly Trp Asn Xaa Asn Ala Xaa Gly Tyr Leu Leu Gly Pro His Ala Val
1               5                   10                  15

Gly Asn His

<210> SEQ ID NO 8
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

-continued

<221> NAME/KEY: MOD_RES
<222> LOCATION: (8),(11)
<223> OTHER INFORMATION: Xaa = methylLanthionine. A single
      methylLanthionine residue represents Abu-S-Ala or Ala-S-Abu and is
      incorporated into the peptide chain at positions 8 and 11

<400> SEQUENCE: 8

Gly Trp Asn Leu Asn Ala Ala Xaa Tyr Leu Xaa Gly Pro His Ala Val
1               5                   10                  15

Gly Asn His Arg
            20

<210> SEQ ID NO 9
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8),(11)
<223> OTHER INFORMATION: Xaa = methylLanthionine. A single
      methylLanthionine residue represents Abu-S-Ala or Ala-S-Abu and is
      incorporated into the peptide chain at positions 8 and 11

<400> SEQUENCE: 9

Gly Trp Asn Leu Asn Ala Ala Xaa Tyr Leu Xaa Gly Pro His Ala Val
1               5                   10                  15

Gly Asn His

<210> SEQ ID NO 10
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8),(12)
<223> OTHER INFORMATION: Xaa = Lanthionine. A single Lanthionine
      residue represents Ala-S-Ala and is incorporated into the peptide
      chain at positions 8 and 12

<400> SEQUENCE: 10

Gly Trp Asn Leu Asn Ala Ala Xaa Tyr Leu Leu Xaa Gly Pro His Ala
1               5                   10                  15

Val Gly Asn His Arg
            20

<210> SEQ ID NO 11
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (8),(12)
<223> OTHER INFORMATION: Xaa = Lanthionine. A single Lanthionine
      residue represents Ala-S-Ala and is incorporated into the peptide
      chain at positions 8 and 12

<400> SEQUENCE: 11

```
Gly Trp Asn Leu Asn Ala Ala Xaa Tyr Leu Leu Xaa Gly Pro His Ala
1               5                   10                  15

Val Gly Asn His
            20

<210> SEQ ID NO 12
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14),(17)
<223> OTHER INFORMATION: Xaa = methylLanthionine.  A single
      methylLanthionine residue represents Abu-S-Ala or Ala-S-Abu and is
      incorporated into the peptide chain at positions 14 and 17

<400> SEQUENCE: 12

Gly Trp Asn Leu Asn Ala Ala Gly Tyr Leu Leu Gly Ala Xaa Ala Val
1               5                   10                  15

Xaa Asn His Arg
            20

<210> SEQ ID NO 13
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14),(17)
<223> OTHER INFORMATION: Xaa = methylLanthionine.  A single
      methylLanthionine residue represents Abu-S-Ala or Ala-S-Abu and is
      incorporated into the peptide chain at positions 14 and 17

<400> SEQUENCE: 13

Gly Trp Asn Leu Asn Ala Ala Gly Tyr Leu Leu Gly Ala Xaa Ala Val
1               5                   10                  15

Xaa Asn His

<210> SEQ ID NO 14
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14),(17)
<223> OTHER INFORMATION: Xaa = Lanthionine.  A single Lanthionine
      residue represents Ala-S-Ala and is incorporated into the peptide
      chain at positions 14 and 17

<400> SEQUENCE: 14

Gly Trp Asn Leu Asn Ala Ala Gly Tyr Leu Leu Gly Ala Xaa Ala Val
1               5                   10                  15

Xaa

<210> SEQ ID NO 15
<211> LENGTH: 20
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14),(17)
<223> OTHER INFORMATION: Xaa = Lanthionine.  A single Lanthionine
      residue represents Ala-S-Ala and is incorporated into the peptide
      chain at positions 14 and 17

<400> SEQUENCE: 15

Gly Trp Asn Leu Asn Ala Ala Gly Tyr Leu Leu Gly Ala Xaa Ala Val
1               5                   10                  15

Xaa Asn His Arg
            20

<210> SEQ ID NO 16
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14),(17)
<223> OTHER INFORMATION: Xaa = Lanthionine.  A single Lanthionine
      residue represents Ala-S-Ala and is incorporated into the peptide
      chain at positions 14 and 17

<400> SEQUENCE: 16

Gly Trp Asn Leu Asn Ala Ala Gly Tyr Leu Leu Gly Ala Xaa Ala Val
1               5                   10                  15

Xaa Asn His

<210> SEQ ID NO 17
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14),(18)
<223> OTHER INFORMATION: Xaa = methylLanthionine.  A single
      methylLanthionine residue represents Abu-S-Ala or Ala-S-Abu and is
      incorporated into the peptide chain at positions 14 and 18

<400> SEQUENCE: 17

Gly Trp Asn Leu Asn Ala Ala Gly Tyr Leu Leu Gly Ala Xaa Ala Val
1               5                   10                  15

Gly Xaa His Arg
            20

<210> SEQ ID NO 18
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
```

```
<222> LOCATION: (14)..(18)
<223> OTHER INFORMATION: Xaa = Lanthionine.  A single Lanthionine
      residue represents Ala-S-Ala and is incorporated into the peptide
      chain at positions 14 and 18

<400> SEQUENCE: 18

Gly Trp Asn Leu Asn Ala Ala Gly Tyr Leu Leu Gly Ala Xaa Ala Val
1               5                   10                  15

Gly Xaa

<210> SEQ ID NO 19
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(18)
<223> OTHER INFORMATION: Xaa = Lanthionine.  A single Lanthionine
      residue represents Ala-S-Ala and is incorporated into the peptide
      chain at positions 14 and 18

<400> SEQUENCE: 19

Gly Trp Asn Leu Asn Ala Ala Gly Tyr Leu Leu Gly Ala Xaa Ala Val
1               5                   10                  15

Gly Xaa His Arg
            20

<210> SEQ ID NO 20
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(19)
<223> OTHER INFORMATION: Xaa = Lanthionine.  A single Lanthionine
      residue represents Ala-S-Ala and is incorporated into the peptide
      chain at positions 14 and 19

<400> SEQUENCE: 20

Gly Trp Asn Leu Asn Ala Ala Gly Tyr Leu Leu Gly Ala Xaa Ala Val
1               5                   10                  15

Gly Asn Xaa Arg
            20

<210> SEQ ID NO 21
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(19)
<223> OTHER INFORMATION: Xaa = Lanthionine.  A single Lanthionine
      residue represents Ala-S-Ala and is incorporated into the peptide
      chain at positions 14 and 19

<400> SEQUENCE: 21

Gly Trp Asn Leu Asn Ala Ala Gly Tyr Leu Leu Gly Ala Xaa Ala Val
```

```
1               5               10              15

Gly Asn Xaa

<210> SEQ ID NO 22
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14),(20)
<223> OTHER INFORMATION: Xaa = Lanthionine.  A single Lanthionine
      residue represents Ala-S-Ala and is incorporated into the peptide
      chain at positions 14 and 20

<400> SEQUENCE: 22

Gly Trp Asn Leu Asn Ala Ala Gly Tyr Leu Leu Gly Ala Xaa Ala Val
1               5                   10                  15

Gly Asn His Xaa
            20

<210> SEQ ID NO 23
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (15),(18)
<223> OTHER INFORMATION: Xaa = methylLanthionine.  A single
      methylLanthionine residue represents Abu-S-Ala or Ala-S-Abu and is
      incorporated into the peptide chain at positions 15 and 18

<400> SEQUENCE: 23

Gly Trp Asn Leu Asn Ala Ala Gly Tyr Leu Leu Gly Pro His Xaa Val
1               5                   10                  15

Gly Xaa His Arg
            20

<210> SEQ ID NO 24
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (15),(18)
<223> OTHER INFORMATION: Xaa = Lanthionine.  A single Lanthionine
      residue represents Ala-S-Ala and is incorporated into the peptide
      chain at positions 15 and 18

<400> SEQUENCE: 24

Gly Trp Asn Leu Asn Ala Ala Gly Tyr Leu Leu Gly Pro His Xaa Val
1               5                   10                  15

Gly Xaa

<210> SEQ ID NO 25
<211> LENGTH: 20
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (16),(19)
<223> OTHER INFORMATION: Xaa = methylLanthionine. A single
      methylLanthionine residue represents Abu-S-Ala or Ala-S-Abu and is
      incorporated into the peptide chain at positions 16 and 19

<400> SEQUENCE: 25

Gly Trp Asn Leu Asn Ala Ala Gly Tyr Leu Leu Gly Pro His Ala Xaa
1               5                   10                  15

Gly Asn Xaa Arg
            20

<210> SEQ ID NO 26
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (16),(19)
<223> OTHER INFORMATION: Xaa = Lanthionine. A single Lanthionine
      residue represents Ala-S-Ala and is incorporated into the peptide
      chain at positions 16 and 19

<400> SEQUENCE: 26

Gly Trp Asn Leu Asn Ala Ala Gly Tyr Leu Leu Gly Pro His Ala Xaa
1               5                   10                  15

Gly Asn Xaa

<210> SEQ ID NO 27
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (15),(20)
<223> OTHER INFORMATION: Xaa = Lanthionine. A single Lanthionine
      residue represents Ala-S-Ala and is incorporated into the peptide
      chain at positions 15 and 20

<400> SEQUENCE: 27

Gly Trp Asn Leu Asn Ala Ala Gly Tyr Leu Leu Gly Ala Ser Xaa Val
1               5                   10                  15

Gly Asn His Xaa
            20

<210> SEQ ID NO 28
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)

```
<223> OTHER INFORMATION: pyro-Glu
<220> FEATURE:
<221> NAME/KEY: MOD_RES
<222> LOCATION: (14),(17)
<223> OTHER INFORMATION: Xaa = methylLanthionine.  A single
      methylLanthionine residue represents Abu-S-Ala or Ala-S-Abu and is
      incorporated into the peptide chain at positions 14 and 17

<400> SEQUENCE: 28

Glu Trp Asn Leu Asn Ala Ala Gly Tyr Leu Leu Gly Ala Xaa Ala Val
1               5                   10                  15

Xaa Asn His Arg
            20

<210> SEQ ID NO 29
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu
<220> FEATURE:
<221> NAME/KEY: MOD_RES
<222> LOCATION: (14),(18)
<223> OTHER INFORMATION: Xaa = methylLanthionine.  A single
      methylLanthionine residue represents Abu-S-Ala or Ala-S-Abu and is
      incorporated into the peptide chain at positions 14 and 18

<400> SEQUENCE: 29

Glu Trp Asn Leu Asn Ala Ala Gly Tyr Leu Leu Gly Ala Xaa Ala Val
1               5                   10                  15

Gly Xaa His Arg
            20

<210> SEQ ID NO 30
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu
<220> FEATURE:
<221> NAME/KEY: MOD_RES
<222> LOCATION: (14),(17)
<223> OTHER INFORMATION: Xaa = methylLanthionine.  A single
      methylLanthionine residue represents Abu-S-Ala or Ala-S-Abu and is
      incorporated into the peptide chain at positions 14 and 17

<400> SEQUENCE: 30

Glu Trp Asn Leu Asn Ala Ala Gly Tyr Leu Leu Gly Ala Xaa Ala Val
1               5                   10                  15

Xaa Asn His

<210> SEQ ID NO 31
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"
<220> FEATURE:
<221> NAME/KEY: MOD_RES
<222> LOCATION: (1)..(1)
<223> OTHER INFORMATION: pyro-Glu
<220> FEATURE:
<221> NAME/KEY: MOD_RES
<222> LOCATION: (14),(17)
<223> OTHER INFORMATION: Xaa = Lanthionine.  A single Lanthionine
    residue represents Ala-S-Ala and is incorporated into the peptide
    chain at positions 14 and 17

<400> SEQUENCE: 31

Glu Trp Asn Leu Asn Ala Ala Gly Tyr Leu Leu Gly Ala Xaa Ala Val
1               5                   10                  15

Xaa

<210> SEQ ID NO 32
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"
<220> FEATURE:
<221> NAME/KEY: MOD_RES
<222> LOCATION: (1)..(1)
<223> OTHER INFORMATION: pyro-Glu
<220> FEATURE:
<221> NAME/KEY: MOD_RES
<222> LOCATION: (8),(12)
<223> OTHER INFORMATION: Xaa = Lanthionine.  A single Lanthionine
    residue represents Ala-S-Ala and is incorporated into the peptide
    chain at positions 8 and 12

<400> SEQUENCE: 32

Glu Trp Asn Leu Asn Ala Ala Xaa Tyr Leu Leu Xaa
1               5                   10

<210> SEQ ID NO 33
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"
<220> FEATURE:
<221> NAME/KEY: MOD_RES
<222> LOCATION: (1)..(1)
<223> OTHER INFORMATION: pyro-Glu
<220> FEATURE:
<221> NAME/KEY: MOD_RES
<222> LOCATION: (15),(18)
<223> OTHER INFORMATION: Xaa = methylLanthionine.  A single
    methylLanthionine residue represents Abu-S-Ala or Ala-S-Abu and is
    incorporated into the peptide chain at positions 15 and 18

<400> SEQUENCE: 33

Glu Trp Asn Leu Asn Ala Ala Gly Tyr Leu Leu Gly Pro His Xaa Val
1               5                   10                  15

Gly Xaa His Arg
            20

<210> SEQ ID NO 34
<211> LENGTH: 17
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"
<220> FEATURE:
<221> NAME/KEY: MOD_RES
<222> LOCATION: (13)..(16)
<223> OTHER INFORMATION: Xaa = methylLanthionine.  A single
      methylLanthionine residue represents Abu-S-Ala or Ala-S-Abu and is
      incorporated into the peptide chain at positions 13 and 16

<400> SEQUENCE: 34

Gly Trp Asn Leu Asn Ala Ala Gly Tyr Leu Leu Gly Xaa His Ala Xaa
1               5                   10                  15

Gly

<210> SEQ ID NO 35
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(17)
<223> OTHER INFORMATION: Xaa = methylLanthionine.  A single
      methylLanthionine residue represents Abu-S-Ala or Ala-S-Abu and is
      incorporated into the peptide chain at positions 14 and 17

<400> SEQUENCE: 35

Gly Trp Asn Leu Asn Ala Ala Gly Tyr Leu Leu Gly Pro Xaa Ala Val
1               5                   10                  15

Xaa

<210> SEQ ID NO 36
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (13)..(16)
<223> OTHER INFORMATION: Xaa = methylLanthionine.  A single
      methylLanthionine residue represents Abu-S-Ala or Ala-S-Abu and is
      incorporated into the peptide chain at positions 13 and 16

<400> SEQUENCE: 36

Gly Trp Asn Leu Asn Ala Ala Gly Tyr Leu Leu Ala Xaa His Ala Xaa
1               5                   10                  15

Gly

<210> SEQ ID NO 37
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(17)
<223> OTHER INFORMATION: Xaa = methylLanthionine.  A single
      methylLanthionine residue represents Abu-S-Ala or Ala-S-Abu and is
      incorporated into the peptide chain at positions 14 and 17

<400> SEQUENCE: 37
```

```
Gly Trp Asn Leu Asn Ala Ala Gly Tyr Leu Leu Gly Ala Xaa Ala Val
1               5                   10                  15

Xaa

<210> SEQ ID NO 38
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu
<220> FEATURE:
<221> NAME/KEY: MOD_RES
<222> LOCATION: (13),(16)
<223> OTHER INFORMATION: Xaa = methylLanthionine.  A single
      methylLanthionine residue represents Abu-S-Ala or Ala-S-Abu and is
      incorporated into the peptide chain at positions 13 and 16

<400> SEQUENCE: 38

Glu Trp Asn Leu Asn Ala Ala Gly Tyr Leu Leu Ala Xaa His Ala Xaa
1               5                   10                  15

Gly

<210> SEQ ID NO 39
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu
<220> FEATURE:
<221> NAME/KEY: MOD_RES
<222> LOCATION: (14),(17)
<223> OTHER INFORMATION: Xaa = methylLanthionine.  A single
      methylLanthionine residue represents Abu-S-Ala or Ala-S-Abu and is
      incorporated into the peptide chain at positions 14 and 17

<400> SEQUENCE: 39

Glu Trp Asn Leu Asn Ala Ala Gly Tyr Leu Leu Gly Ala Xaa Ala Val
1               5                   10                  15

Xaa

<210> SEQ ID NO 40
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu
<220> FEATURE:
<221> NAME/KEY: MOD_RES
<222> LOCATION: (13),(16)
<223> OTHER INFORMATION: Xaa = Lanthionine.  A single Lanthionine
      residue represents Ala-S-Ala and is incorporated into the peptide
      chain at positions 13 and 16
```

-continued

<400> SEQUENCE: 40

Glu Trp Asn Leu Asn Ala Ala Gly Tyr Leu Leu Ala Xaa His Ala Xaa
1               5                   10                  15

Gly

<210> SEQ ID NO 41
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu
<220> FEATURE:
<221> NAME/KEY: MOD_RES
<222> LOCATION: (13),(16)
<223> OTHER INFORMATION: Xaa = methylLanthionine.  A single
      methylLanthionine residue represents Abu-S-Ala or Ala-S-Abu and is
      incorporated into the peptide chain at positions 13 and 16

<400> SEQUENCE: 41

Glu Trp Asn Leu Asn Ala Ala Gly Tyr Leu Leu Ala Xaa His Ala Xaa
1               5                   10                  15

Gly Asn His Arg
            20

<210> SEQ ID NO 42
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu
<220> FEATURE:
<221> NAME/KEY: MOD_RES
<222> LOCATION: (16),(19)
<223> OTHER INFORMATION: Xaa = methylLanthionine.  A single
      methylLanthionine residue represents Abu-S-Ala or Ala-S-Abu and is
      incorporated into the peptide chain at positions 16 and 19

<400> SEQUENCE: 42

Glu Trp Asn Leu Asn Ala Ala Gly Tyr Leu Leu Gly Pro His Ala Xaa
1               5                   10                  15

Gly Asn Xaa Arg
            20

<210> SEQ ID NO 43
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14),(17)
<223> OTHER INFORMATION: Xaa = methylLanthionine.  A single
      methylLanthionine residue represents Abu-S-Ala or Ala-S-Abu and is
      incorporated into the peptide chain at positions 14 and 17

<400> SEQUENCE: 43

Gly Trp Asn Val Asn Ala Ala Gly Tyr Leu Leu Gly Ala Xaa Ala Val
1               5                   10                  15

Xaa Asn His Arg
            20

<210> SEQ ID NO 44
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14),(17)
<223> OTHER INFORMATION: Xaa = methylLanthionine.  A single
      methylLanthionine residue represents Abu-S-Ala or Ala-S-Abu and is
      incorporated into the peptide chain at positions 14 and 17

<400> SEQUENCE: 44

Gly Trp Asn Asp Asn Ala Ala Gly Tyr Leu Leu Gly Ala Xaa Ala Val
1               5                   10                  15

Xaa Asn His Arg
            20

<210> SEQ ID NO 45
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14),(17)
<223> OTHER INFORMATION: Xaa = methylLanthionine.  A single
      methylLanthionine residue represents Abu-S-Ala or Ala-S-Abu and is
      incorporated into the peptide chain at positions 14 and 17

<400> SEQUENCE: 45

Gly Trp Asn Asn Asn Ala Ala Gly Tyr Leu Leu Gly Ala Xaa Ala Val
1               5                   10                  15

Xaa Asn His Arg
            20

<210> SEQ ID NO 46
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14),(17)
<223> OTHER INFORMATION: Xaa = methylLanthionine.  A single
      methylLanthionine residue represents Abu-S-Ala or Ala-S-Abu and is
      incorporated into the peptide chain at positions 14 and 17

<400> SEQUENCE: 46

Gly Trp Asn Leu Val Ala Ala Gly Tyr Leu Leu Gly Ala Xaa Ala Val
1               5                   10                  15

Xaa Asn His Arg

```
<210> SEQ ID NO 47
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14),(17)
<223> OTHER INFORMATION: Xaa = methylLanthionine.  A single
      methylLanthionine residue represents Abu-S-Ala or Ala-S-Abu and is
      incorporated into the peptide chain at positions 14 and 17

<400> SEQUENCE: 47

Gly Trp Asn Leu Lys Ala Ala Gly Tyr Leu Leu Gly Ala Xaa Ala Val
1               5                   10                  15

Xaa Asn His Arg
            20

<210> SEQ ID NO 48
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14),(17)
<223> OTHER INFORMATION: Xaa = methylLanthionine.  A single
      methylLanthionine residue represents Abu-S-Ala or Ala-S-Abu and is
      incorporated into the peptide chain at positions 14 and 17

<400> SEQUENCE: 48

Gly Trp Asn Leu Asp Ala Ala Gly Tyr Leu Leu Gly Ala Xaa Ala Val
1               5                   10                  15

Xaa Asn His Arg
            20

<210> SEQ ID NO 49
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14),(17)
<223> OTHER INFORMATION: Xaa = methylLanthionine.  A single
      methylLanthionine residue represents Abu-S-Ala or Ala-S-Abu and is
      incorporated into the peptide chain at positions 14 and 17

<400> SEQUENCE: 49

Gly Trp Asn Leu Gln Ala Ala Gly Tyr Leu Leu Gly Ala Xaa Ala Val
1               5                   10                  15

Xaa Asn His Arg
            20

<210> SEQ ID NO 50
<211> LENGTH: 17
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu
<220> FEATURE:
<221> NAME/KEY: MOD_RES
<222> LOCATION: (14),(17)
<223> OTHER INFORMATION: Xaa = Lanthionine.  A single Lanthionine
      residue represents Ala-S-Ala and is incorporated into the peptide
      chain at positions 14 and 17

<400> SEQUENCE: 50

Glu Trp Asn Leu Asn Ala Ala Gly Tyr Leu Leu Gly Pro Xaa Ala Val
1               5                   10                  15

Xaa

<210> SEQ ID NO 51
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu
<220> FEATURE:
<221> NAME/KEY: MOD_RES
<222> LOCATION: (8),(12)
<223> OTHER INFORMATION: Xaa = Lanthionine.  A single Lanthionine
      residue represents Ala-S-Ala and is incorporated into the peptide
      chain at positions 8 and 12

<400> SEQUENCE: 51

Glu Trp Thr Leu Asn Ala Ala Xaa Tyr Leu Leu Xaa
1               5                   10

<210> SEQ ID NO 52
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu
<220> FEATURE:
<221> NAME/KEY: MOD_RES
<222> LOCATION: (14),(17)
<223> OTHER INFORMATION: Xaa = methylLanthionine.  A single
      methylLanthionine residue represents Abu-S-Ala or Ala-S-Abu and is
      incorporated into the peptide chain at positions 14 and 17

<400> SEQUENCE: 52

Glu Trp Asn Leu Asn Ala Ala Gly Tyr Leu Leu Gly Pro Xaa Ala Val
1               5                   10                  15

Xaa

<210> SEQ ID NO 53
<211> LENGTH: 12
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu
<220> FEATURE:
<221> NAME/KEY: MOD_RES
<222> LOCATION: (8),(12)
<223> OTHER INFORMATION: Xaa = methylLanthionine.  A single
      methylLanthionine residue represents Abu-S-Ala or Ala-S-Abu and is
      incorporated into the peptide chain at positions 8 and 12

<400> SEQUENCE: 53

Glu Trp Thr Leu Asn Ala Ala Xaa Tyr Leu Leu Xaa
1               5                   10

<210> SEQ ID NO 54
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu
<220> FEATURE:
<221> NAME/KEY: MOD_RES
<222> LOCATION: (8)..(8)
<223> OTHER INFORMATION: D-Cys

<400> SEQUENCE: 54

Glu Trp Asn Leu Asn Ala Ala Cys Tyr Leu Leu Cys
1               5                   10

<210> SEQ ID NO 55
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu
<220> FEATURE:
<221> NAME/KEY: MOD_RES
<222> LOCATION: (14)..(14)
<223> OTHER INFORMATION: D-Cys

<400> SEQUENCE: 55

Glu Trp Asn Leu Asn Ala Ala Gly Tyr Leu Leu Gly Ala Cys Ala Val
1               5                   10                  15

Cys

<210> SEQ ID NO 56
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
```

```
<222> LOCATION: (1)..(1)
<223> OTHER INFORMATION: pyro-Glu
<220> FEATURE:
<221> NAME/KEY: MOD_RES
<222> LOCATION: (15)..(15)
<223> OTHER INFORMATION: D-Cys

<400> SEQUENCE: 56

Glu Trp Asn Leu Asn Ala Ala Gly Tyr Leu Leu Gly Pro His Cys Val
1               5                   10                  15

Gly Cys

<210> SEQ ID NO 57
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu
<220> FEATURE:
<221> NAME/KEY: MOD_RES
<222> LOCATION: (16)..(16)
<223> OTHER INFORMATION: D-Cys

<400> SEQUENCE: 57

Glu Trp Asn Leu Asn Ala Ala Gly Tyr Leu Leu Gly Pro His Ala Cys
1               5                   10                  15

Gly Asn Cys

<210> SEQ ID NO 58
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gly Trp Asn Thr Asn Ala Cys Gly Tyr Leu Leu Gly Pro His Ala Val
1               5                   10                  15

Gly Asn His Arg
            20

<210> SEQ ID NO 59
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gly Trp Asn Thr Asn Ala Cys Gly Tyr Leu Leu Gly Pro His Ala Val
1               5                   10                  15

Gly Asn His

<210> SEQ ID NO 60
<211> LENGTH: 20
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 60

Gly Trp Asn Leu Asn Ala Ala Thr Tyr Leu Cys Gly Pro His Ala Val
1               5                   10                  15

Gly Asn His Arg
            20

<210> SEQ ID NO 61
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gly Trp Asn Leu Asn Ala Ala Thr Tyr Leu Cys Gly Pro His Ala Val
1               5                   10                  15

Gly Asn His

<210> SEQ ID NO 62
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Gly Trp Asn Leu Asn Ala Ala Ser Tyr Leu Leu Cys Gly Pro His Ala
1               5                   10                  15

Val Gly Asn His Arg
            20

<210> SEQ ID NO 63
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gly Trp Asn Leu Asn Ala Ala Ser Tyr Leu Leu Cys Gly Pro His Ala
1               5                   10                  15

Val Gly Asn His
            20

<210> SEQ ID NO 64
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Gly Trp Asn Leu Asn Ala Ala Gly Tyr Leu Leu Gly Ala Thr Ala Val
```

<210> SEQ ID NO 65
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 65

Gly Trp Asn Leu Asn Ala Ala Gly Tyr Leu Leu Gly Ala Thr Ala Val
1               5                   10                  15

Cys Asn His

<210> SEQ ID NO 66
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 66

Gly Trp Asn Leu Asn Ala Ala Gly Tyr Leu Leu Gly Ala Ser Ala Val
1               5                   10                  15

Cys

<210> SEQ ID NO 67
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 67

Gly Trp Asn Leu Asn Ala Ala Gly Tyr Leu Leu Gly Ala Ser Ala Val
1               5                   10                  15

Cys Asn His Arg
            20

<210> SEQ ID NO 68
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 68

Gly Trp Asn Leu Asn Ala Ala Gly Tyr Leu Leu Gly Ala Ser Ala Val
1               5                   10                  15

Cys Asn His

<210> SEQ ID NO 69
<211> LENGTH: 20
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 69

Gly Trp Asn Leu Asn Ala Ala Gly Tyr Leu Leu Gly Ala Thr Ala Val
1               5                   10                  15

Gly Cys His Arg
            20

<210> SEQ ID NO 70
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Gly Trp Asn Leu Asn Ala Ala Gly Tyr Leu Leu Gly Ala Ser Ala Val
1               5                   10                  15

Gly Cys

<210> SEQ ID NO 71
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Gly Trp Asn Leu Asn Ala Ala Gly Tyr Leu Leu Gly Ala Ser Ala Val
1               5                   10                  15

Gly Cys His Arg
            20

<210> SEQ ID NO 72
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Gly Trp Asn Leu Asn Ala Ala Gly Tyr Leu Leu Gly Ala Ser Ala Val
1               5                   10                  15

Gly Asn Cys Arg
            20

<210> SEQ ID NO 73
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Gly Trp Asn Leu Asn Ala Ala Gly Tyr Leu Leu Gly Ala Ser Ala Val
```

-continued

```
1               5                   10                  15

Gly Asn Cys

<210> SEQ ID NO 74
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Gly Trp Asn Leu Asn Ala Ala Gly Tyr Leu Leu Gly Ala Ser Ala Val
1               5                   10                  15

Gly Asn His Cys
            20

<210> SEQ ID NO 75
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Gly Trp Asn Leu Asn Ala Ala Gly Tyr Leu Leu Gly Pro His Thr Val
1               5                   10                  15

Gly Cys His Arg
            20

<210> SEQ ID NO 76
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Gly Trp Asn Leu Asn Ala Ala Gly Tyr Leu Leu Gly Pro His Ser Val
1               5                   10                  15

Gly Cys

<210> SEQ ID NO 77
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

Gly Trp Asn Leu Asn Ala Ala Gly Tyr Leu Leu Gly Pro His Ala Thr
1               5                   10                  15

Gly Asn Cys Arg
            20

<210> SEQ ID NO 78
<211> LENGTH: 19
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

Gly Trp Asn Leu Asn Ala Ala Gly Tyr Leu Leu Gly Pro His Ala Ser
1               5                   10                  15

Gly Asn Cys

<210> SEQ ID NO 79
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Gln Trp Asn Leu Asn Ala Ala Gly Tyr Leu Leu Gly Ala Thr Ala Val
1               5                   10                  15

Cys Asn His Arg
            20

<210> SEQ ID NO 80
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Gln Trp Asn Leu Asn Ala Ala Gly Tyr Leu Leu Gly Ala Thr Ala Val
1               5                   10                  15

Cys Asn His

<210> SEQ ID NO 81
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Gln Trp Asn Leu Asn Ala Ala Gly Tyr Leu Leu Gly Ala Ser Ala Val
1               5                   10                  15

Cys

<210> SEQ ID NO 82
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Gln Trp Asn Leu Asn Ala Ala Ser Tyr Leu Leu Cys
1               5                   10
```

<210> SEQ ID NO 83
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Gln Trp Asn Leu Asn Ala Ala Gly Tyr Leu Leu Gly Pro His Thr Val
1               5                   10                  15

Gly Cys His Arg
            20

<210> SEQ ID NO 84
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Gly Trp Asn Leu Asn Ala Ala Gly Tyr Leu Leu Gly Thr His Ala Cys
1               5                   10                  15

Gly

<210> SEQ ID NO 85
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 85

Gly Trp Asn Leu Asn Ala Ala Gly Tyr Leu Leu Gly Pro Thr Ala Val
1               5                   10                  15

Cys

<210> SEQ ID NO 86
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 86

Gly Trp Asn Leu Asn Ala Ala Gly Tyr Leu Leu Ala Thr His Ala Cys
1               5                   10                  15

Gly

<210> SEQ ID NO 87
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 87

Gly Trp Asn Leu Asn Ala Ala Gly Tyr Leu Leu Gly Ala Thr Ala Val
1               5                   10                  15

Cys

<210> SEQ ID NO 88
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Gln Trp Asn Leu Asn Ala Ala Gly Tyr Leu Leu Ala Thr His Ala Cys
1               5                   10                  15

Gly

<210> SEQ ID NO 89
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu

<400> SEQUENCE: 89

Glu Trp Asn Leu Asn Ala Ala Gly Tyr Leu Leu Gly Ala Thr Ala Val
1               5                   10                  15

Cys

<210> SEQ ID NO 90
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Gln Trp Asn Leu Asn Ala Ala Gly Tyr Leu Leu Ala Ser His Ala Cys
1               5                   10                  15

Gly

<210> SEQ ID NO 91
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Gln Trp Asn Leu Asn Ala Ala Gly Tyr Leu Leu Ala Thr His Ala Cys
1               5                   10                  15

Gly Asn His Arg
```

```
<210> SEQ ID NO 92
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Gln Trp Asn Leu Asn Ala Ala Gly Tyr Leu Leu Gly Pro His Ala Thr
1               5                   10                  15

Gly Asn Cys Arg
            20

<210> SEQ ID NO 93
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Gln Trp Asn Leu Asn Ala Ala Gly Tyr Leu Leu Gly Ala Thr Ala Val
1               5                   10                  15

Cys

<210> SEQ ID NO 94
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Gly Trp Asn Val Asn Ala Ala Gly Tyr Leu Leu Gly Ala Thr Ala Val
1               5                   10                  15

Cys Asn His Arg
            20

<210> SEQ ID NO 95
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Gly Trp Asn Asp Asn Ala Ala Gly Tyr Leu Leu Gly Ala Thr Ala Val
1               5                   10                  15

Cys Asn His Arg
            20

<210> SEQ ID NO 96
<211> LENGTH: 20
<212> TYPE: PRT
<213> ORGANISM: Artificial Sequence
<220> FEATURE:
```

-continued

<221> NAME/KEY: source
<223> OTHER INFORMATION: /note="Description of Artificial Sequence:
      Synthetic peptide"

<400> SEQUENCE: 96

Gly Trp Asn Asn Asn Ala Ala Gly Tyr Leu Leu Gly Ala Thr Ala Val
1               5                   10                  15

Cys Asn His Arg
            20

<210> SEQ ID NO 97
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Gly Trp Asn Leu Val Ala Ala Gly Tyr Leu Leu Gly Ala Thr Ala Val
1               5                   10                  15

Cys Asn His Arg
            20

<210> SEQ ID NO 98
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Gly Trp Asn Leu Lys Ala Ala Gly Tyr Leu Leu Gly Ala Thr Ala Val
1               5                   10                  15

Cys Asn His Arg
            20

<210> SEQ ID NO 99
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Gly Trp Asn Leu Asp Ala Ala Gly Tyr Leu Leu Gly Ala Thr Ala Val
1               5                   10                  15

Cys Asn His Arg
            20

<210> SEQ ID NO 100
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Gly Trp Asn Leu Gln Ala Ala Gly Tyr Leu Leu Gly Ala Thr Ala Val

Cys Asn His Arg
            20

<210> SEQ ID NO 101
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Gln Trp Asn Leu Asn Ala Ala Gly Tyr Leu Leu Gly Pro Thr Ala Val
1               5                   10                  15

Cys

<210> SEQ ID NO 102
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Gln Trp Thr Leu Asn Ala Ala Thr Tyr Leu Leu Cys
1               5                   10

<210> SEQ ID NO 103
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Gln Trp Asn Leu Asn Ala Ala Gly Tyr Leu Leu Gly Pro Ser Ala Val
1               5                   10                  15

Cys

<210> SEQ ID NO 104
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 104

Gln Trp Thr Leu Asn Ala Ala Ser Tyr Leu Leu Cys
1               5                   10

<210> SEQ ID NO 105
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

-continued

```
<400> SEQUENCE: 105

Met Ser Thr Lys Asp Phe Asn Leu Asp Leu Val Ser Val Ser Lys Lys
1               5                   10                  15

Asp Ser Gly Ala Ser Pro Arg
            20

<210> SEQ ID NO 106
<211> LENGTH: 30
<212> TYPE: PRT
<213> ORGANISM: Unknown
<220> FEATURE:
<221> NAME/KEY: source
<223> OTHER INFORMATION: /note="Description of Unknown: Galanin
      polypeptide"

<400> SEQUENCE: 106

Gly Trp Asn Leu Asn Ala Ala Gly Tyr Leu Leu Gly Pro His Ala Val
1               5                   10                  15

Gly Asn His Arg Ser Phe Ser Asp Lys Asn Gly Leu Thr Ser
            20                  25                  30

<210> SEQ ID NO 107
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Gly Trp Thr Leu Asn Ser Ala Gly Tyr Leu Leu Gly Pro His Ala
1               5                   10                  15

<210> SEQ ID NO 108
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Gly Trp Asn Leu Asn Ala Ala Gly Tyr Leu Leu Gly Pro His Ala Val
1               5                   10                  15

Gly Asn His Arg
            20

<210> SEQ ID NO 109
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Gly Trp Asn Leu Asn Ala Ala Gly Tyr Leu Leu Ala Thr His Ala Cys
1               5                   10                  15

Gly Asn His Arg
            20

<210> SEQ ID NO 110
```

```
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu

<400> SEQUENCE: 110

Glu Trp Asn Leu Asn Ala Ala Gly Tyr Leu Leu Ala Thr His Ala Cys
1               5                   10                  15

Gly Asn His Arg
            20

<210> SEQ ID NO 111
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu

<400> SEQUENCE: 111

Glu Trp Asn Leu Asn Ala Ala Gly Tyr Leu Leu Gly Ala Thr Ala Val
1               5                   10                  15

Cys Asn His Arg
            20

<210> SEQ ID NO 112
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu

<400> SEQUENCE: 112

Glu Trp Asn Leu Asn Ala Ala Gly Tyr Leu Leu Gly Ala Thr Ala Val
1               5                   10                  15

Cys Asn His

<210> SEQ ID NO 113
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu

<400> SEQUENCE: 113
```

```
Glu Trp Asn Leu Asn Ala Ala Gly Tyr Leu Leu Gly Pro His Ala Thr
1               5                   10                  15

Gly Asn Cys Arg
            20

<210> SEQ ID NO 114
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu

<400> SEQUENCE: 114

Glu Trp Asn Leu Asn Ala Ala Gly Tyr Leu Leu Gly Ala Thr Ala Val
1               5                   10                  15

Gly Cys His Arg
            20

<210> SEQ ID NO 115
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu

<400> SEQUENCE: 115

Glu Trp Asn Leu Asn Ala Ala Ser Tyr Leu Leu Cys
1               5                   10

<210> SEQ ID NO 116
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu

<400> SEQUENCE: 116

Glu Trp Asn Leu Asn Ala Ala Gly Tyr Leu Leu Gly Pro His Thr Val
1               5                   10                  15

Gly Cys His Arg
            20

<210> SEQ ID NO 117
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: MOD_RES
<222> LOCATION: (1)..(1)
<223> OTHER INFORMATION: pyro-Glu

<400> SEQUENCE: 117

Glu Trp Asn Leu Asn Ala Ala Gly Tyr Leu Leu Gly Pro Thr Ala Val
1               5                   10                  15

Cys

<210> SEQ ID NO 118
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: pyro-Glu

<400> SEQUENCE: 118

Glu Trp Asn Leu Asn Ala Ala Gly Tyr Leu Leu Ala Thr His Ala Cys
1               5                   10                  15

Gly

<210> SEQ ID NO 119
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Gly Trp Asn Leu Asn Lys Ala Gly Tyr Leu Leu Gly Pro His Ala Val
1               5                   10                  15

Gly Asn His Arg
            20

<210> SEQ ID NO 120
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Gly Trp Asn Leu Asn Asp Ala Gly Tyr Leu Leu Gly Pro His Ala Val
1               5                   10                  15

Gly Asn His Arg
            20

<210> SEQ ID NO 121
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121
```

```
Gly Trp Asn Leu Asn Leu Ala Gly Tyr Leu Leu Gly Pro His Ala Val
1               5                   10                  15

Gly Asn His Arg
            20

<210> SEQ ID NO 122
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 122

Gly Trp Asn Leu Asn Trp Ala Gly Tyr Leu Leu Gly Pro His Ala Val
1               5                   10                  15

Gly Asn His Arg
            20

<210> SEQ ID NO 123
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Gly Trp Asn Leu Asn Ala Ala Lys Tyr Leu Leu Gly Pro His Ala Val
1               5                   10                  15

Gly Asn His Arg
            20

<210> SEQ ID NO 124
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Gly Trp Asn Leu Asn Ala Ala Asp Tyr Leu Leu Gly Pro His Ala Val
1               5                   10                  15

Gly Asn His Arg
            20

<210> SEQ ID NO 125
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Gly Trp Asn Leu Asn Ala Ala Gln Tyr Leu Leu Gly Pro His Ala Val
1               5                   10                  15

Gly Asn His Arg
            20
```

<210> SEQ ID NO 126
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 126

Gly Trp Asn Leu Asn Ala Ala Pro Tyr Leu Leu Gly Pro His Ala Val
1               5                   10                  15

Gly Asn His Arg
            20

<210> SEQ ID NO 127
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (14)..(14)
<223> OTHER INFORMATION: D-Cys

<400> SEQUENCE: 127

Gln Trp Asn Leu Asn Ala Ala Gly Tyr Leu Leu Gly Pro Cys Ala Val
1               5                   10                  15

Cys

<210> SEQ ID NO 128
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (8)..(8)
<223> OTHER INFORMATION: D-Cys

<400> SEQUENCE: 128

Gln Trp Thr Leu Asn Ala Ala Cys Tyr Leu Leu Cys
1               5                   10